(12) United States Patent
Dumbauld

(10) Patent No.: US 7,935,052 B2
(45) Date of Patent: *May 3, 2011

(54) FORCEPS WITH SPRING LOADED END EFFECTOR ASSEMBLY

(75) Inventor: Patrick L. Dumbauld, Lyons, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 1114 days.

This patent is subject to a terminal disclaimer.

(21) Appl. No.: 11/706,015

(22) Filed: Feb. 14, 2007

(65) Prior Publication Data

US 2007/0142834 A1 Jun. 21, 2007

(51) Int. Cl.
*A61B 17/00* (2006.01)

(52) U.S. Cl. .............. 600/205; 606/46; 606/51; 606/52; 606/206; 606/207

(58) Field of Classification Search .................. 600/104; 606/50–52
See application file for complete search history.

(56) References Cited

U.S. PATENT DOCUMENTS

| | | |
|---|---|---|
| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,176,479 A | 10/1939 | Willis |
| 2,305,156 A | 4/1941 | Grubel |
| 2,279,753 A | 4/1942 | Knopp |
| 2,327,353 A | 8/1943 | Karle |
| 2,632,661 A | 8/1948 | Cristofv |
| 2,668,538 A | 2/1954 | Baker |
| 2,796,065 A | 6/1957 | Kapp |

(Continued)

FOREIGN PATENT DOCUMENTS

CA 2104423 2/1994

(Continued)

OTHER PUBLICATIONS

Sigel et al. "The Mechanism of Blood Vessel Closure by High Frequency Electrocoagulation" Surgery Gynecology & Obstetrics, Oct. 1965 pp. 823-831.

(Continued)

*Primary Examiner* — Matthew J Kasztejna

(57) ABSTRACT

An endoscopic forceps for treating tissue includes a handle assembly having a elongated shaft extending therefrom that is movable relative to the handle assembly by an actuator. The forceps also includes an end effector assembly with first and second jaw members that are movable about a pivot for clamping tissue. Each of the jaw members include: an insulative housing having an electrically conductive, inwardly facing tissue contacting surface and a flange with a camming surface. The flange includes a spring-like tail that mounts at least partially within the distal end of the elongated shaft to bias the jaw members in an open configuration. A proximal portion of the spring-like tail is biased radially outward within the distal end of the elongated shaft. The actuator is movable to actuate the elongated shaft to cam the flanges to pivot the jaw members to clamp tissue.

5 Claims, 4 Drawing Sheets

U.S. PATENT DOCUMENTS

| | | |
|---|---|---|
| 3,073,311 A | 1/1963 | Tibbs et al. |
| 3,372,288 A | 3/1968 | Wigington |
| 3,459,187 A | 8/1969 | Pallotta |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,233,734 A | 11/1980 | Bies |
| 4,236,470 A | 12/1980 | Stenson |
| 4,300,564 A | 11/1981 | Furihata |
| 4,311,145 A | 1/1982 | Esty et al. |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,147,357 A | 9/1992 | Rose et al. |
| 5,151,102 A | 9/1992 | Xamiyama et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,314,445 A | 5/1994 | Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,374,277 A | 12/1994 | Hassler |
| 5,376,089 A | 12/1994 | Smith |
| 5,383,875 A | 1/1995 | Bays et al. |
| 5,383,897 A | 1/1995 | Wholey |
| 5,389,098 A | 2/1995 | Tsuruta et al. |
| 5,389,103 A | 2/1995 | Melzer et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,403,342 A | 4/1995 | Tovey et al. |
| 5,405,344 A | 4/1995 | Williamson et al. |
| 5,409,763 A | 4/1995 | Serizawa et al. |
| 5,411,519 A | 5/1995 | Tovey et al. |
| 5,411,520 A | 5/1995 | Nash et al. |

| Patent | Type | Date | Inventor |
|---|---|---|---|
| 5,413,571 | A | 5/1995 | Katsaros et al. |
| 5,415,656 | A | 5/1995 | Tihon et al. |
| 5,415,657 | A | 5/1995 | Taymor-Luria |
| 5,422,567 | A | 6/1995 | Matsunaga |
| 5,423,810 | A | 6/1995 | Goble et al. |
| 5,425,690 | A | 6/1995 | Chang |
| 5,425,739 | A | 6/1995 | Jessen |
| 5,429,616 | A | 7/1995 | Schaffer |
| 5,431,672 | A | 7/1995 | Cote et al. |
| 5,431,674 | A | 7/1995 | Basile et al. |
| 5,437,292 | A | 8/1995 | Kipshidze et al. |
| 5,438,302 | A | 8/1995 | Goble |
| 5,439,478 | A | 8/1995 | Palmer |
| 5,441,517 | A | 8/1995 | Kensey et al. |
| 5,443,463 | A | 8/1995 | Stern et al. |
| 5,443,464 | A | 8/1995 | Russell et al. |
| 5,443,480 | A | 8/1995 | Jacobs et al. |
| 5,445,638 | A | 8/1995 | Rydell et al. |
| 5,445,658 | A | 8/1995 | Durrfeld et al. |
| 5,449,480 | A | 9/1995 | Kuriya et al. |
| 5,451,224 | A | 9/1995 | Goble et al. |
| 5,454,823 | A | 10/1995 | Richardson et al. |
| 5,454,827 | A | 10/1995 | Aust et al. |
| 5,456,684 | A | 10/1995 | Schmidt et al. |
| 5,458,598 | A * | 10/1995 | Feinberg et al. ................. 606/52 |
| 5,460,629 | A | 10/1995 | Shlain et al. |
| 5,461,765 | A | 10/1995 | Linden et al. |
| 5,462,546 | A | 10/1995 | Rydell |
| 5,472,442 | A | 12/1995 | Klicek |
| 5,472,443 | A | 12/1995 | Cordis et al. |
| 5,478,351 | A | 12/1995 | Meade et al. |
| 5,480,406 | A | 1/1996 | Nolan et al. |
| 5,480,409 | A | 1/1996 | Riza |
| 5,484,436 | A | 1/1996 | Eggers et al. |
| 5,496,312 | A | 3/1996 | Klicek |
| 5,496,317 | A | 3/1996 | Goble et al. |
| 5,496,347 | A | 3/1996 | Hashiguchi et al. |
| 5,499,997 | A | 3/1996 | Sharpe et al. |
| 5,499,998 | A * | 3/1996 | Meade ......................... 606/207 |
| 5,509,922 | A | 4/1996 | Aranyi et al. |
| 5,514,134 | A | 5/1996 | Rydell et al. |
| 5,527,313 | A | 6/1996 | Scott et al. |
| 5,528,833 | A | 6/1996 | Sakuma |
| 5,529,067 | A | 6/1996 | Larsen et al. |
| 5,531,744 | A | 7/1996 | Nardella et al. |
| 5,536,251 | A | 7/1996 | Evard et al. |
| 5,540,684 | A | 7/1996 | Hassler, Jr. |
| 5,540,685 | A | 7/1996 | Parins et al. |
| 5,540,706 | A | 7/1996 | Aust et al. |
| 5,540,715 | A | 7/1996 | Katsaros et al. |
| 5,542,945 | A | 8/1996 | Fritzsch |
| 5,558,671 | A | 9/1996 | Yates |
| 5,558,672 | A | 9/1996 | Edwards et al. |
| 5,562,619 | A | 10/1996 | Mirarchi et al. |
| 5,562,699 | A | 10/1996 | Heimberger et al. |
| 5,562,720 | A | 10/1996 | Stern et al. |
| 5,564,615 | A | 10/1996 | Bishop et al. |
| 5,569,241 | A | 10/1996 | Edwards |
| 5,569,243 | A | 10/1996 | Kortenbach et al. |
| 5,571,100 | A | 11/1996 | Goble et al. |
| 5,573,424 | A | 11/1996 | Poppe |
| 5,573,534 | A | 11/1996 | Stone |
| 5,573,535 | A | 11/1996 | Viklund |
| 5,575,799 | A | 11/1996 | Bolanos et al. |
| 5,575,805 | A | 11/1996 | Li |
| 5,578,052 | A | 11/1996 | Koros et al. |
| 5,579,781 | A | 12/1996 | Cooke |
| 5,582,611 | A | 12/1996 | Tsukagoshi et al. |
| 5,582,617 | A | 12/1996 | Klieman et al. |
| 5,585,896 | A | 12/1996 | Yamazaki et al. |
| 5,590,570 | A | 1/1997 | LeMaire, III et al. |
| 5,591,181 | A | 1/1997 | Stone et al. |
| 5,597,107 | A | 1/1997 | Knodel et al. |
| 5,601,224 | A | 2/1997 | Bishop et al. |
| 5,601,601 | A | 2/1997 | Tal et al. |
| 5,601,641 | A | 2/1997 | Stephens |
| 5,603,711 | A | 2/1997 | Parins et al. |
| 5,603,723 | A | 2/1997 | Aranyi et al. |
| 5,611,798 | A | 3/1997 | Eggers |
| 5,611,808 | A | 3/1997 | Hossain et al. |
| 5,611,813 | A | 3/1997 | Lichtman |
| 5,620,415 | A | 4/1997 | Lucey et al. |
| 5,620,453 | A | 4/1997 | Nallakrishnan |
| 5,620,459 | A | 4/1997 | Lichtman |
| 5,624,452 | A | 4/1997 | Yates |
| 5,626,578 | A | 5/1997 | Tihon |
| 5,626,609 | A | 5/1997 | Zvenyatsky et al. |
| 5,630,833 | A | 5/1997 | Katsaros et al. |
| 5,637,110 | A | 6/1997 | Pennybacker et al. |
| 5,638,003 | A | 6/1997 | Hall |
| 5,643,294 | A | 7/1997 | Tovey et al. |
| 5,647,869 | A | 7/1997 | Goble et al. |
| 5,647,871 | A | 7/1997 | Levine et al. |
| 5,649,959 | A | 7/1997 | Hannam et al. |
| 5,655,650 | A | 8/1997 | Naitou |
| 5,658,281 | A | 8/1997 | Heard |
| D384,413 | S | 9/1997 | Zlock et al. |
| 5,662,667 | A | 9/1997 | Knodel |
| 5,665,100 | A | 9/1997 | Yoon |
| 5,667,526 | A | 9/1997 | Levin |
| 5,674,220 | A | 10/1997 | Fox et al. |
| 5,674,229 | A | 10/1997 | Tovey et al. |
| 5,681,282 | A | 10/1997 | Eggers et al. |
| 5,688,270 | A | 11/1997 | Yates et al. |
| 5,690,652 | A | 11/1997 | Wurster et al. |
| 5,690,653 | A | 11/1997 | Richardson et al. |
| 5,693,051 | A | 12/1997 | Schulze et al. |
| 5,693,920 | A | 12/1997 | Maeda |
| 5,695,522 | A | 12/1997 | LeMaire, III et al. |
| 5,700,261 | A | 12/1997 | Brinkerhoff |
| 5,700,270 | A | 12/1997 | Peyser et al. |
| 5,702,390 | A | 12/1997 | Austin et al. |
| 5,707,369 | A | 1/1998 | Vaitekunas et al. |
| 5,709,680 | A | 1/1998 | Yates et al. |
| 5,716,366 | A | 2/1998 | Yates |
| 5,720,744 | A | 2/1998 | Eggleston et al. |
| 5,722,421 | A | 3/1998 | Francese et al. |
| 5,725,536 | A | 3/1998 | Oberlin et al. |
| 5,727,428 | A | 3/1998 | LeMaire, III et al. |
| 5,735,848 | A | 4/1998 | Yates et al. |
| 5,743,906 | A | 4/1998 | Parins et al. |
| 5,746,570 | A * | 5/1998 | Gujda et al. ................ 414/795.6 |
| 5,752,973 | A | 5/1998 | Kieturakis |
| 5,755,717 | A | 5/1998 | Yates et al. |
| 5,759,188 | A | 6/1998 | Yoon |
| 5,766,130 | A | 6/1998 | Selmonosky |
| 5,766,166 | A | 6/1998 | Hooven |
| 5,766,170 | A | 6/1998 | Eggers |
| 5,766,196 | A | 6/1998 | Griffiths |
| 5,769,849 | A | 6/1998 | Eggers |
| 5,772,655 | A | 6/1998 | Bauer et al. |
| 5,772,670 | A | 6/1998 | Brosa |
| 5,776,128 | A | 7/1998 | Eggers |
| 5,776,130 | A | 7/1998 | Buysse et al. |
| 5,779,646 | A | 7/1998 | Koblish et al. |
| 5,779,701 | A | 7/1998 | McBrayer et al. |
| H1745 | H | 8/1998 | Paraschac |
| 5,792,137 | A | 8/1998 | Carr et al. |
| 5,792,165 | A | 8/1998 | Klieman et al. |
| 5,792,177 | A | 8/1998 | Kaseda |
| 5,797,537 | A | 8/1998 | Oberlin et al. |
| 5,797,927 | A | 8/1998 | Yoon |
| 5,797,938 | A | 8/1998 | Paraschac et al. |
| 5,797,941 | A | 8/1998 | Schulze et al. |
| 5,797,958 | A | 8/1998 | Yoon |
| 5,800,449 | A * | 9/1998 | Wales ........................... 606/172 |
| 5,807,393 | A | 9/1998 | Williamson, IV et al. |
| 5,810,764 | A | 9/1998 | Eggers et al. |
| 5,810,805 | A | 9/1998 | Sutcu et al. |
| 5,810,808 | A | 9/1998 | Eggers |
| 5,810,811 | A | 9/1998 | Yates et al. |
| 5,810,877 | A | 9/1998 | Roth et al. |
| 5,814,043 | A | 9/1998 | Shapeton |
| 5,814,054 | A | 9/1998 | Kortenbach et al. |
| 5,817,093 | A | 10/1998 | Williamson, IV et al. |
| 5,817,119 | A | 10/1998 | Klieman et al. |
| 5,820,630 | A | 10/1998 | Lind |
| 5,824,978 | A | 10/1998 | Karasik et al. |

| Patent Number | Kind | Date | Inventor(s) |
|---|---|---|---|
| 5,827,271 | A | 10/1998 | Buysse et al. |
| 5,827,279 | A | 10/1998 | Hughett et al. |
| 5,827,281 | A | 10/1998 | Levin |
| 5,827,323 | A | 10/1998 | Klieman et al. |
| 5,827,548 | A | 10/1998 | Lavallee et al. |
| 5,833,690 | A | 11/1998 | Yates et al. |
| 5,843,080 | A | 12/1998 | Fleenor et al. |
| 5,849,022 | A | 12/1998 | Sakashita et al. |
| 5,853,412 | A | 12/1998 | Mayenberger |
| 5,859,527 | A | 1/1999 | Cook |
| 5,860,976 | A | 1/1999 | Billings et al. |
| 5,876,401 | A | 3/1999 | Schulze et al. |
| 5,876,412 | A | 3/1999 | Piraka |
| 5,882,567 | A | 3/1999 | Cavallaro et al. |
| 5,891,141 | A | 4/1999 | Rydell |
| 5,891,142 | A | 4/1999 | Eggers et al. |
| 5,893,863 | A | 4/1999 | Yoon |
| 5,893,875 | A | 4/1999 | O'Connor et al. |
| 5,893,877 | A | 4/1999 | Gampp, Jr. et al. |
| 5,897,563 | A | 4/1999 | Yoon et al. |
| 5,902,301 | A | 5/1999 | Olig |
| 5,906,630 | A | 5/1999 | Anderhub et al. |
| 5,908,420 | A | 6/1999 | Parins et al. |
| 5,908,432 | A | 6/1999 | Pan |
| 5,911,719 | A | 6/1999 | Eggers |
| 5,913,874 | A | 6/1999 | Berns et al. |
| 5,921,916 | A | 7/1999 | Aeikens et al. |
| 5,921,984 | A | 7/1999 | Sutcu et al. |
| 5,925,043 | A | 7/1999 | Kumar et al. |
| 5,928,136 | A | 7/1999 | Barry |
| 5,935,126 | A | 8/1999 | Riza |
| 5,941,869 | A | 8/1999 | Patterson et al. |
| 5,944,718 | A | 8/1999 | Dafforn et al. |
| 5,951,546 | A | 9/1999 | Lorentzen |
| 5,951,549 | A | 9/1999 | Richardson et al. |
| 5,954,720 | A | 9/1999 | Wilson et al. |
| 5,954,731 | A | 9/1999 | Yoon |
| 5,954,733 | A | 9/1999 | Yoon |
| 5,957,923 | A | 9/1999 | Hahnen et al. |
| 5,957,937 | A | 9/1999 | Yoon |
| 5,960,544 | A | 10/1999 | Beyers |
| 5,961,514 | A | 10/1999 | Long et al. |
| 5,964,758 | A | 10/1999 | Dresden |
| 5,976,132 | A | 11/1999 | Morris |
| 5,984,932 | A | 11/1999 | Yoon |
| 5,984,938 | A | 11/1999 | Yoon |
| 5,984,939 | A | 11/1999 | Yoon |
| 5,989,277 | A | 11/1999 | LeMaire, III et al. |
| 5,993,466 | A | 11/1999 | Yoon |
| 5,993,467 | A | 11/1999 | Yoon |
| 5,997,565 | A | 12/1999 | Inoue |
| 6,004,332 | A | 12/1999 | Yoon et al. |
| 6,004,335 | A | 12/1999 | Vaitekunas et al. |
| 6,010,516 | A | 1/2000 | Hulka et al. |
| 6,017,358 | A | 1/2000 | Yoon et al. |
| 6,021,693 | A | 2/2000 | Feng-Sing |
| 6,024,741 | A | 2/2000 | Williamson et al. |
| 6,024,743 | A | 2/2000 | Edwards |
| 6,024,744 | A | 2/2000 | Kese et al. |
| 6,027,522 | A | 2/2000 | Palmer |
| 6,030,384 | A | 2/2000 | Nezhat |
| 6,033,399 | A | 3/2000 | Gines |
| 6,039,733 | A | 3/2000 | Buysse et al. |
| 6,041,679 | A | 3/2000 | Slater et al. |
| 6,050,996 | A | 4/2000 | Schmaltz et al. |
| 6,053,914 | A | 4/2000 | Eggers et al. |
| 6,053,933 | A | 4/2000 | Balazs et al. |
| D424,694 | S | 5/2000 | Tetzlaff et al. |
| D425,201 | S | 5/2000 | Tetzlaff et al. |
| 6,059,782 | A | 5/2000 | Novak et al. |
| 6,066,139 | A | 5/2000 | Ryan et al. |
| 6,074,386 | A | 6/2000 | Goble et al. |
| 6,077,287 | A | 6/2000 | Taylor et al. |
| 6,080,180 | A | 6/2000 | Yoon et al. |
| RE36,795 | E | 7/2000 | Rydell |
| 6,083,223 | A | 7/2000 | Baker |
| 6,086,586 | A | 7/2000 | Hooven |
| 6,086,601 | A | 7/2000 | Yoon |
| 6,090,107 | A | 7/2000 | Borgmeier et al. |
| 6,096,037 | A | 8/2000 | Mulier et al. |
| 6,099,550 | A | 8/2000 | Yoon |
| 6,102,909 | A | 8/2000 | Chen et al. |
| 6,106,542 | A | 8/2000 | Toybin et al. |
| 6,110,171 | A | 8/2000 | Rydell |
| 6,113,596 | A | 9/2000 | Hooven et al. |
| 6,113,598 | A | 9/2000 | Baker |
| 6,117,158 | A | 9/2000 | Measamer et al. |
| 6,122,549 | A | 9/2000 | Sharkey et al. |
| 6,123,701 | A | 9/2000 | Nezhat |
| H1904 | H | 10/2000 | Yates et al. |
| 6,126,658 | A | 10/2000 | Baker |
| 6,126,665 | A | 10/2000 | Yoon |
| 6,139,563 | A | 10/2000 | Cosgrove, III et al. |
| 6,143,005 | A | 11/2000 | Yoon et al. |
| 6,152,923 | A | 11/2000 | Ryan |
| 6,162,220 | A | 12/2000 | Nezhat |
| 6,171,316 | B1 | 1/2001 | Kovac et al. |
| 6,174,309 | B1 | 1/2001 | Wrublewski et al. |
| 6,178,628 | B1 | 1/2001 | Clemens et al. |
| 6,179,834 | B1 | 1/2001 | Buysse et al. |
| 6,179,837 | B1 | 1/2001 | Hooven |
| 6,183,467 | B1 | 2/2001 | Shapeton et al. |
| 6,187,003 | B1 | 2/2001 | Buysse et al. |
| 6,190,386 | B1 | 2/2001 | Rydell |
| 6,190,400 | B1 | 2/2001 | Vandemoer et al. |
| 6,193,718 | B1 | 2/2001 | Kortenbach et al. |
| 6,206,876 | B1 | 3/2001 | Levine et al. |
| 6,206,877 | B1 | 3/2001 | Kese et al. |
| 6,206,893 | B1 | 3/2001 | Klein et al. |
| 6,214,028 | B1 | 4/2001 | Yoon et al. |
| 6,217,602 | B1 | 4/2001 | Redmon |
| 6,217,615 | B1 | 4/2001 | Sioshansi et al. |
| 6,221,039 | B1 | 4/2001 | Durgin et al. |
| 6,223,100 | B1 | 4/2001 | Green |
| 6,224,593 | B1 | 5/2001 | Ryan et al. |
| 6,224,614 | B1 | 5/2001 | Yoon |
| 6,228,080 | B1 | 5/2001 | Gines |
| 6,228,083 | B1 | 5/2001 | Lands et al. |
| 6,248,124 | B1 | 6/2001 | Pedros et al. |
| 6,248,944 | B1 | 6/2001 | Ito |
| 6,261,307 | B1 | 7/2001 | Yoon et al. |
| 6,267,761 | B1 | 7/2001 | Ryan |
| 6,270,497 | B1 | 8/2001 | Sekino et al. |
| 6,270,508 | B1 | 8/2001 | Klieman et al. |
| 6,273,887 | B1 | 8/2001 | Yamauchi et al. |
| 6,277,117 | B1 | 8/2001 | Tetzlaff et al. |
| 6,280,458 | B1 | 8/2001 | Boche et al. |
| 6,283,961 | B1 | 9/2001 | Underwood et al. |
| D449,886 | S | 10/2001 | Tetzlaff et al. |
| 6,298,550 | B1 | 10/2001 | Kirwan |
| 6,302,424 | B1 | 10/2001 | Gisinger et al. |
| 6,319,262 | B1 | 11/2001 | Bates et al. |
| 6,319,451 | B1 | 11/2001 | Brune |
| 6,322,561 | B1 | 11/2001 | Eggers et al. |
| 6,322,580 | B1 | 11/2001 | Kanner |
| 6,325,795 | B1 | 12/2001 | Lindemann et al. |
| 6,334,860 | B1 | 1/2002 | Dorn |
| 6,334,861 | B1 | 1/2002 | Chandler et al. |
| 6,345,532 | B1 | 2/2002 | Coudray et al. |
| 6,350,264 | B1 | 2/2002 | Hooven |
| 6,352,536 | B1 | 3/2002 | Buysse et al. |
| 6,358,249 | B1 | 3/2002 | Chen et al. |
| 6,358,259 | B1 | 3/2002 | Swain et al. |
| 6,358,268 | B1 | 3/2002 | Hunt et al. |
| 6,364,879 | B1 | 4/2002 | Chen et al. |
| D457,958 | S | 5/2002 | Dycus et al. |
| D457,959 | S | 5/2002 | Tetzlaff et al. |
| 6,387,094 | B1 | 5/2002 | Eitenmuller |
| 6,391,035 | B1 | 5/2002 | Appleby et al. |
| 6,398,779 | B1 | 6/2002 | Buysse et al. |
| 6,402,747 | B1 | 6/2002 | Lindemann et al. |
| 6,409,728 | B1 | 6/2002 | Ehr et al. |
| H2037 | H | 7/2002 | Yates et al. |
| 6,419,675 | B1 | 7/2002 | Gallo, Sr. |
| 6,425,896 | B1 | 7/2002 | Baltschun et al. |
| 6,432,112 | B2 | 8/2002 | Brock et al. |
| 6,440,144 | B1 | 8/2002 | Bacher |
| 6,443,952 | B1 | 9/2002 | Mulier et al. |

| | | | | | |
|---|---|---|---|---|---|
| 6,443,970 B1 | 9/2002 | Schulze et al. | 6,790,217 B2 | 9/2004 | Schulze et al. |
| 6,451,018 B1 | 9/2002 | Lands et al. | 6,796,981 B2 | 9/2004 | Wham et al. |
| 6,458,125 B1 | 10/2002 | Cosmescu | D496,997 S | 10/2004 | Dycus et al. |
| 6,458,128 B1 | 10/2002 | Schulze | 6,800,825 B1 | 10/2004 | Sasaki et al. |
| 6,458,130 B1 | 10/2002 | Frazier et al. | 6,802,843 B2 | 10/2004 | Truckai et al. |
| 6,461,352 B2 | 10/2002 | Morgan et al. | 6,808,525 B2 | 10/2004 | Latterell et al. |
| 6,461,368 B2 | 10/2002 | Fogarty et al. | D499,181 S | 11/2004 | Dycus et al. |
| 6,464,701 B1 | 10/2002 | Hooven et al. | 6,818,000 B2 | 11/2004 | Muller et al. |
| 6,464,702 B2 | 10/2002 | Schulze et al. | 6,821,285 B2 | 11/2004 | Laufer et al. |
| 6,464,704 B2 | 10/2002 | Schmaltz et al. | 6,835,200 B2 | 12/2004 | Laufer et al. |
| 6,485,489 B2 | 11/2002 | Teirstein et al. | 6,857,357 B2 | 2/2005 | Fujii |
| 6,494,888 B1 | 12/2002 | Laufer et al. | 6,860,880 B2 | 3/2005 | Treat et al. |
| 6,500,176 B1 | 12/2002 | Truckai et al. | 6,887,240 B1 | 5/2005 | Lands et al. |
| 6,506,196 B1 | 1/2003 | Laufer | 6,889,116 B2 | 5/2005 | Jinno |
| 6,508,815 B1 | 1/2003 | Strul et al. | 6,914,201 B2 | 7/2005 | Van Vooren et al. |
| 6,511,480 B1 | 1/2003 | Tetzlaff et al. | 6,926,716 B2 | 8/2005 | Baker et al. |
| 6,514,215 B1 | 2/2003 | Ouchi | 6,929,644 B2 | 8/2005 | Truckai et al. |
| 6,514,252 B2 | 2/2003 | Nezhat et al. | 6,932,810 B2 | 8/2005 | Ryan |
| 6,517,539 B1 | 2/2003 | Smith et al. | 6,932,816 B2 | 8/2005 | Phan |
| 6,527,771 B1 | 3/2003 | Weadock et al. | 6,934,134 B2 | 8/2005 | Mori et al. |
| 6,533,784 B2 | 3/2003 | Truckai et al. | 6,936,061 B2 | 8/2005 | Sasaki |
| 6,545,239 B2 | 4/2003 | Spedale et al. | D509,297 S | 9/2005 | Wells |
| 6,558,385 B1 | 5/2003 | McClurken et al. | 6,942,662 B2 | 9/2005 | Goble et al. |
| 6,562,037 B2 | 5/2003 | Paton et al. | 6,943,311 B2 | 9/2005 | Miyako |
| 6,569,105 B1 | 5/2003 | Kortenbach et al. | 6,953,430 B2 | 10/2005 | Kidooka |
| 6,582,450 B2 | 6/2003 | Ouchi | 6,953,461 B2 | 10/2005 | McClurken et al. |
| 6,585,735 B1 | 7/2003 | Frazier et al. | 6,958,070 B2 | 10/2005 | Witt et al. |
| 6,602,252 B2 | 8/2003 | Mollenauer | 6,960,210 B2 | 11/2005 | Lands et al. |
| 6,605,790 B2 | 8/2003 | Yoshida | 6,964,662 B2 | 11/2005 | Kidooka |
| 6,616,658 B2 | 9/2003 | Ineson | 6,966,907 B2 | 11/2005 | Goble |
| 6,616,661 B2 | 9/2003 | Wellman et al. | 6,972,017 B2 | 12/2005 | Smith et al. |
| 6,620,161 B2 | 9/2003 | Schulze et al. | 6,977,495 B2 | 12/2005 | Donofrio |
| 6,620,184 B2 | 9/2003 | De Laforcade et al. | 6,979,786 B2 | 12/2005 | Aukland et al. |
| 6,626,901 B1 | 9/2003 | Treat et al. | 6,981,628 B2 | 1/2006 | Wales |
| 6,638,287 B2 | 10/2003 | Danitz et al. | 6,987,244 B2 | 1/2006 | Bauer |
| 6,641,595 B1 | 11/2003 | Moran et al. | 6,994,707 B2 | 2/2006 | Ellman et al. |
| 6,652,514 B2 | 11/2003 | Ellman et al. | 6,994,709 B2 | 2/2006 | Iida |
| 6,652,521 B2 | 11/2003 | Schulze | 6,997,931 B2 | 2/2006 | Sauer et al. |
| 6,656,175 B2 | 12/2003 | Francischelli et al. | 7,001,381 B2 | 2/2006 | Harano et al. |
| 6,656,177 B2 | 12/2003 | Truckai et al. | 7,011,657 B2 | 3/2006 | Truckai et al. |
| 6,660,072 B2 | 12/2003 | Chatterjee | 7,033,354 B2 | 4/2006 | Keppel |
| 6,663,639 B1 | 12/2003 | Laufer et al. | 7,033,356 B2 | 4/2006 | Latterell et al. |
| 6,663,641 B1 | 12/2003 | Kovac et al. | 7,041,102 B2 | 5/2006 | Truckai et al. |
| 6,666,854 B1 | 12/2003 | Lange | 7,044,948 B2 | 5/2006 | Keppel |
| 6,669,696 B2 | 12/2003 | Bacher et al. | 7,052,489 B2 | 5/2006 | Griego et al. |
| 6,673,092 B1 | 1/2004 | Bacher | 7,052,496 B2 | 5/2006 | Yamauchi |
| 6,676,660 B2 | 1/2004 | Wampler et al. | 7,063,715 B2 | 6/2006 | Onuki et al. |
| 6,676,676 B2 | 1/2004 | Danitz et al. | D525,361 S | 7/2006 | Hushka |
| 6,679,882 B1 | 1/2004 | Kornerup | 7,070,597 B2 | 7/2006 | Truckai et al. |
| 6,682,527 B2 | 1/2004 | Strul | 7,083,618 B2 | 8/2006 | Couture et al. |
| 6,682,528 B2 | 1/2004 | Frazier et al. | 7,083,619 B2 | 8/2006 | Truckai et al. |
| 6,685,724 B1 | 2/2004 | Haluck | 7,083,620 B2 | 8/2006 | Jahns et al. |
| 6,689,131 B2 | 2/2004 | McClurken | 7,087,051 B2 | 8/2006 | Bourne et al. |
| 6,692,445 B2 | 2/2004 | Roberts et al. | 7,087,054 B2 | 8/2006 | Truckai et al. |
| 6,693,246 B1 | 2/2004 | Rudolph et al. | 7,090,673 B2 | 8/2006 | Dycus et al. |
| 6,695,840 B2 | 2/2004 | Schulze | 7,090,689 B2 | 8/2006 | Nagase et al. |
| 6,702,810 B2 | 3/2004 | McClurken et al. | 7,101,371 B2 | 9/2006 | Dycus et al. |
| 6,723,092 B2 | 4/2004 | Brown et al. | 7,101,372 B2 | 9/2006 | Dycus et al. |
| 6,726,068 B2 | 4/2004 | Miller | 7,101,373 B2 | 9/2006 | Dycus et al. |
| 6,726,686 B2 | 4/2004 | Buysse et al. | 7,103,947 B2 | 9/2006 | Sartor et al. |
| 6,726,694 B2 | 4/2004 | Blatter et al. | 7,107,124 B2 | 9/2006 | Green |
| 6,733,498 B2 | 5/2004 | Paton et al. | 7,112,199 B2 | 9/2006 | Cosmescu |
| 6,736,813 B2 | 5/2004 | Yamauchi et al. | D531,311 S | 10/2006 | Guerra et al. |
| 6,743,229 B2 | 6/2004 | Buysse et al. | 7,115,123 B2 | 10/2006 | Knowlton et al. |
| 6,743,230 B2 | 6/2004 | Lutze et al. | 7,118,570 B2 | 10/2006 | Tetzlaff et al. |
| 6,743,239 B1 | 6/2004 | Kuehn et al. | 7,118,587 B2 | 10/2006 | Dycus et al. |
| 6,743,240 B2 | 6/2004 | Smith et al. | 7,131,860 B2 | 11/2006 | Sartor et al. |
| 6,755,843 B2 | 6/2004 | Chung et al. | 7,131,970 B2 | 11/2006 | Moses et al. |
| 6,756,553 B1 | 6/2004 | Yamaguchi et al. | 7,131,971 B2 | 11/2006 | Dycus et al. |
| 6,757,977 B2 | 7/2004 | Dambal et al. | 7,135,020 B2 | 11/2006 | Lawes et al. |
| D493,888 S | 8/2004 | Reschke | D533,942 S | 12/2006 | Kerr et al. |
| 6,770,072 B1 | 8/2004 | Truckai et al. | 7,145,757 B2 | 12/2006 | Shea et al. |
| 6,773,409 B2 | 8/2004 | Truckai et al. | 7,147,638 B2 | 12/2006 | Chapman et al. |
| 6,773,432 B1 | 8/2004 | Clayman et al. | 7,150,097 B2 | 12/2006 | Sremcich et al. |
| 6,773,434 B2 | 8/2004 | Ciarrocca | 7,150,749 B2 | 12/2006 | Dycus et al. |
| 6,773,441 B1 | 8/2004 | Laufer et al. | 7,153,314 B2 | 12/2006 | Laufer et al. |
| 6,775,575 B2 | 8/2004 | Bommannan et al. | D535,027 S | 1/2007 | James et al. |
| 6,776,780 B2 | 8/2004 | Mulier et al. | 7,156,842 B2 | 1/2007 | Sartor et al. |
| 6,786,905 B2 | 9/2004 | Swanson et al. | 7,156,846 B2 | 1/2007 | Dycus et al. |

| Patent No. | Date | Inventor |
|---|---|---|
| 7,160,298 B2 | 1/2007 | Lawes et al. |
| 7,160,299 B2 | 1/2007 | Baily |
| 7,169,146 B2 | 1/2007 | Truckai et al. |
| 7,179,255 B2 | 2/2007 | Lettice et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al |
| 7,223,264 B2 | 5/2007 | Daniel et al. |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,244,257 B2 | 7/2007 | Podhajsky et al. |
| 7,246,734 B2 | 7/2007 | Shelton, IV |
| 7,248,944 B2 | 7/2007 | Green |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,311,709 B2 | 12/2007 | Truckai et al. |
| 7,314,471 B2 | 1/2008 | Holman |
| 7,318,823 B2 | 1/2008 | Sharps et al. |
| 7,329,256 B2 | 2/2008 | Johnson et al. |
| 7,329,257 B2 | 2/2008 | Kanehira et al. |
| D564,662 S | 3/2008 | Moses et al. |
| 7,338,526 B2 | 3/2008 | Steinberg |
| 7,342,754 B2 | 3/2008 | Fitzgerald et al. |
| 7,344,268 B2 | 3/2008 | Jigamian |
| D567,943 S | 4/2008 | Moses et al. |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,336 B2 | 7/2008 | Orszulak et al. |
| D575,395 S | 8/2008 | Hushka |
| D575,401 S | 8/2008 | Hixson et al. |
| 7,435,249 B2 | 10/2008 | Buysse et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,458,972 B2 | 12/2008 | Keppel |
| 7,473,253 B2 | 1/2009 | Dycus et al. |
| 7,481,810 B2 | 1/2009 | Dumbauld et al. |
| 7,487,780 B2 | 2/2009 | Hooven |
| 7,491,201 B2 | 2/2009 | Shields et al. |
| 7,491,202 B2 | 2/2009 | Odom et al. |
| 7,500,975 B2 | 3/2009 | Cunningham et al. |
| 7,510,556 B2 | 3/2009 | Nguyen et al. |
| 7,513,898 B2 | 4/2009 | Johnson et al. |
| 7,540,872 B2 | 6/2009 | Schechter et al. |
| 7,549,995 B2 | 6/2009 | Schultz |
| 7,553,312 B2 | 6/2009 | Tetzlaff et al. |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1* | 12/2002 | Couture et al. ................ 606/51 |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069570 A1 | 4/2003 | Witzel et al. |
| 2003/0069571 A1 | 4/2003 | Treat et al. |
| 2003/0078578 A1 | 4/2003 | Truckai et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158548 A1 | 8/2003 | Phan et al. |
| 2003/0158549 A1 | 8/2003 | Swanson |
| 2003/0171747 A1 | 9/2003 | Kanehira et al. |
| 2003/0181910 A1 | 9/2003 | Dycus et al. |
| 2003/0199869 A1 | 10/2003 | Johnson et al. |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2003/0236325 A1 | 12/2003 | Bonora |
| 2003/0236518 A1 | 12/2003 | Marchitto et al. |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0122423 A1 | 6/2004 | Dycus et al. |
| 2004/0143263 A1 | 7/2004 | Schechter et al. |
| 2004/0147925 A1 | 7/2004 | Buysse et al. |
| 2004/0148035 A1 | 7/2004 | Barrett et al. |
| 2004/0162557 A1 | 8/2004 | Tetzlaff et al. |
| 2004/0193153 A1 | 9/2004 | Sartor et al. |
| 2004/0199181 A1 | 10/2004 | Knodel et al. |
| 2004/0210282 A1 | 10/2004 | Flock et al. |
| 2004/0224590 A1 | 11/2004 | Rawa et al. |
| 2004/0230189 A1 | 11/2004 | Keppel |
| 2004/0236326 A1 | 11/2004 | Schulze et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0260281 A1 | 12/2004 | Baxter, III et al. |
| 2005/0004564 A1 | 1/2005 | Wham et al. |
| 2005/0004569 A1 | 1/2005 | Witt et al. |
| 2005/0021025 A1 | 1/2005 | Buysse et al. |
| 2005/0021027 A1 | 1/2005 | Shields et al. |
| 2005/0033278 A1 | 2/2005 | McClurken et al. |
| 2005/0059934 A1 | 3/2005 | Wenchell et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0107784 A1 | 5/2005 | Moses et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0113827 A1 | 5/2005 | Dumbauld et al. |
| 2005/0113828 A1 | 5/2005 | Shields et al. |
| 2005/0149017 A1 | 7/2005 | Dycus |
| 2005/0149151 A1 | 7/2005 | Orszulak et al. |
| 2005/0154387 A1 | 7/2005 | Moses et al. |
| 2005/0187547 A1 | 8/2005 | Sugi |
| 2005/0197659 A1 | 9/2005 | Bahney |
| 2005/0203504 A1 | 9/2005 | Wham et al. |
| 2005/0240179 A1 | 10/2005 | Buysse et al. |
| 2006/0052778 A1 | 3/2006 | Chapman et al. |
| 2006/0052779 A1 | 3/2006 | Hammill |
| 2006/0064085 A1 | 3/2006 | Schechter et al. |
| 2006/0064086 A1 | 3/2006 | Odom |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0079933 A1 | 4/2006 | Hushka et al. |
| 2006/0084973 A1 | 4/2006 | Hushka |
| 2006/0089670 A1 | 4/2006 | Hushka |
| 2006/0116675 A1 | 6/2006 | McClurken et al. |
| 2006/0129146 A1 | 6/2006 | Dycus et al. |
| 2006/0161150 A1 | 7/2006 | Keppel |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189980 A1 | 8/2006 | Johnson et al. |
| 2006/0190035 A1 | 8/2006 | Hushka et al. |
| 2006/0217709 A1 | 9/2006 | Couture et al. |
| 2006/0224158 A1 | 10/2006 | Odom et al. |
| 2006/0229666 A1 | 10/2006 | Suzuki et al. |
| 2006/0253126 A1 | 11/2006 | Bjerken et al. |

| Publication No. | Date | Inventor |
|---|---|---|
| 2006/0259036 A1 | 11/2006 | Tetzlaff et al. |
| 2006/0264922 A1 | 11/2006 | Sartor et al. |
| 2006/0264931 A1 | 11/2006 | Chapman et al. |
| 2006/0271038 A1 | 11/2006 | Johnson et al. |
| 2006/0283093 A1 | 12/2006 | Petrovic et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0055231 A1 | 3/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0198011 A1 | 8/2007 | Sugita |
| 2007/0203485 A1 | 8/2007 | Keppel |
| 2007/0213706 A1 | 9/2007 | Dumbauld et al. |
| 2007/0213707 A1 | 9/2007 | Dumbauld et al. |
| 2007/0213708 A1 | 9/2007 | Dumbauld et al. |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1 | 1/2008 | Odom |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039835 A1 | 2/2008 | Johnson et al. |
| 2008/0039836 A1 | 2/2008 | Odom et al. |
| 2008/0045947 A1 | 2/2008 | Johnson et al. |
| 2008/0058802 A1 | 3/2008 | Couture et al. |
| 2008/0082100 A1 | 4/2008 | Orton et al. |
| 2008/0091189 A1 | 4/2008 | Carlton |
| 2008/0114356 A1 | 5/2008 | Johnson et al. |
| 2008/0167651 A1 | 7/2008 | Tetzlaff et al. |
| 2008/0195093 A1 | 8/2008 | Couture et al. |
| 2008/0215051 A1 | 9/2008 | Buysse et al. |
| 2008/0243120 A1 | 10/2008 | Lawes et al. |
| 2008/0249527 A1 | 10/2008 | Couture |
| 2008/0312653 A1 | 12/2008 | Arts et al. |
| 2008/0319442 A1 | 12/2008 | Unger et al. |
| 2009/0012520 A1 | 1/2009 | Hixson et al. |
| 2009/0018535 A1 | 1/2009 | Schechter et al. |
| 2009/0024126 A1 | 1/2009 | Artale et al. |
| 2009/0043304 A1 | 2/2009 | Tetzlaff et al. |
| 2009/0048596 A1 | 2/2009 | Shields et al. |
| 2009/0062794 A1 | 3/2009 | Buysse et al. |
| 2009/0082766 A1 | 3/2009 | Unger et al. |
| 2009/0082767 A1 | 3/2009 | Unger et al. |
| 2009/0082769 A1 | 3/2009 | Unger et al. |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0088748 A1 | 4/2009 | Guerra et al. |
| 2009/0088749 A1 | 4/2009 | Hushka et al. |
| 2009/0088750 A1 | 4/2009 | Hushka et al. |
| 2009/0112206 A1 | 4/2009 | Dumbauld et al. |
| 2009/0131934 A1 | 5/2009 | Odom et al. |
| 2009/0149853 A1 | 6/2009 | Shields et al. |
| 2009/0149854 A1 | 6/2009 | Cunningham et al. |
| 2009/0171350 A1 | 7/2009 | Dycus et al. |
| 2009/0171353 A1 | 7/2009 | Johnson et al. |
| 2009/0182327 A1 | 7/2009 | Unger |
| 2009/0187188 A1 | 7/2009 | Guerra et al. |

FOREIGN PATENT DOCUMENTS

| | | |
|---|---|---|
| DE | 2415263 | 10/1975 |
| DE | 2514501 | 10/1976 |
| DE | 2627679 | 1/1977 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 19738457 | 1/2009 |
| EP | 0364216 A1 | 4/1990 |
| EP | 0467501 | 1/1992 |
| EP | 518230 A1 | 12/1992 |
| EP | 0 541 930 B1 | 5/1993 |
| EP | 0572131 | 12/1993 |
| EP | 584787 A1 | 3/1994 |
| EP | 0589453 A2 | 3/1994 |
| EP | 0589555 | 3/1994 |
| EP | 0623316 A1 | 11/1994 |
| EP | 0624348 A2 | 11/1994 |
| EP | 0650701 A1 | 5/1995 |
| EP | 0694290 A3 | 3/1996 |
| EP | 0717966 A1 | 6/1996 |
| EP | 0754437 A3 | 3/1997 |
| EP | 0517243 | 9/1997 |
| EP | 853922 A1 | 7/1998 |
| EP | 0875209 A1 | 11/1998 |
| EP | 0878169 A1 | 11/1998 |
| EP | 0887046 A3 | 1/1999 |
| EP | 0923907 A1 | 6/1999 |
| EP | 0986990 A1 | 3/2000 |
| EP | 1034747 A1 | 9/2000 |
| EP | 1034748 A1 | 9/2000 |
| EP | 1025807 A3 | 10/2000 |
| EP | 1034746 A3 | 10/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1082944 A1 | 3/2001 |
| EP | 1159926 A2 | 12/2001 |
| EP | 1177771 | 2/2002 |
| EP | 1301135 A | 4/2003 |
| EP | 1330991 A1 | 7/2003 |
| EP | 1486177 A2 | 6/2004 |
| EP | 1472984 A1 | 11/2004 |
| EP | 0774232 | 1/2005 |
| EP | 1527747 A2 | 5/2005 |
| EP | 1530952 A1 | 5/2005 |
| EP | 1532932 A1 | 5/2005 |
| EP | 1535581 A2 | 6/2005 |
| EP | 1609430 A1 | 12/2005 |
| EP | 1632192 A1 | 3/2006 |
| EP | 1642543 | 4/2006 |
| EP | 1645238 A1 | 4/2006 |
| EP | 1645240 A2 | 4/2006 |
| EP | 1649821 | 4/2006 |
| EP | 1707143 A1 | 10/2006 |
| EP | 1769765 | 4/2007 |
| EP | 1769766 | 4/2007 |
| EP | 1929970 | 6/2008 |
| EP | 1683496 | 12/2008 |
| GB | 623316 | 5/1949 |

| | | |
|---|---|---|
| GB | 1490585 | 11/1977 |
| GB | 2214430 A | 6/1989 |
| GB | 2213416 | 8/1989 |
| JP | 501068 | 9/1984 |
| JP | 502328 | 3/1992 |
| JP | 5-5106 | 1/1993 |
| JP | 5-40112 | 2/1993 |
| JP | 06343644 A2 | 12/1994 |
| JP | 07265328 A2 | 10/1995 |
| JP | 08056955 A2 | 3/1996 |
| JP | 08252263 A2 | 10/1996 |
| JP | 09010223 A2 | 1/1997 |
| JP | 11244298 A2 | 9/1999 |
| JP | 2000342599 A2 | 12/2000 |
| JP | 2000350732 A2 | 12/2000 |
| JP | 2001008944 A2 | 1/2001 |
| JP | 2001029356 A2 | 2/2001 |
| JP | 2001128990 A2 | 5/2001 |
| SU | 401367 | 11/1974 |
| WO | WO 89/00757 | 1/1989 |
| WO | WO 92/04873 | 4/1992 |
| WO | WO 92/06642 | 4/1992 |
| WO | WO 93/21845 | 11/1993 |
| WO | WO 94/08524 A | 4/1994 |
| WO | WO 94/20025 | 9/1994 |
| WO | WO 95/02369 | 1/1995 |
| WO | WO 95/07662 | 3/1995 |
| WO | WO 95/15124 | 6/1995 |
| WO | WO 96/05776 | 2/1996 |
| WO | WO 96/22056 | 7/1996 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 | 3/1999 |
| WO | WO 99/23933 | 5/1999 |
| WO | WO 99/40857 | 8/1999 |
| WO | WO 99/40861 | 8/1999 |
| WO | WO 99/51158 | 10/1999 |
| WO | WO 99/66850 A | 12/1999 |
| WO | WO 00/24330 | 5/2000 |
| WO | WO 00/24331 | 5/2000 |
| WO | WO 00/36986 | 6/2000 |
| WO | WO 00/41638 | 7/2000 |
| WO | WO 00/47124 | 8/2000 |
| WO | WO 00/53112 | 9/2000 |
| WO | WO 01/17448 A | 3/2001 |
| WO | WO 01/54604 | 8/2001 |
| WO | WO 02/07627 | 1/2002 |
| WO | WO 02/067798 A1 | 9/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 03/061500 | 7/2003 |
| WO | WO 03/090630 A3 | 11/2003 |
| WO | WO 03/101311 | 12/2003 |
| WO | WO 2004/032776 A1 | 4/2004 |
| WO | WO 2004/032777 | 4/2004 |
| WO | WO 2004/052221 | 6/2004 |
| WO | WO 2004/073488 A2 | 9/2004 |
| WO | WO 2004/073490 | 9/2004 |
| WO | WO 2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 A1 | 1/2005 |
| WO | WO 2005/004735 | 1/2005 |
| WO | WO 2005/110264 | 11/2005 |
| WO | WO 2008/045348 | 4/2008 |
| WO | WO 2008/045350 | 4/2008 |

OTHER PUBLICATIONS

Bergdahl et al. "Studies on Coagulation and the Development of an Automatic Computerized Bipolar Coagulator" J.Neurosurg, vol. 75, Jul. 1991, pp. 148-151.

Kennedy et al. "High-burst-strength, feedback-controlled bipolar vessel sealing" Surgical Endoscopy (1998) 12: 876-878.

Peterson et al, "Comparison of Healing Process Following Ligation with Sutures and Bipolar Vessel Sealing" Surgical Technology International (2001).

Linehan et al. "A Phase I Study of the LigaSure Vessel Sealing System in Hepatic Surgery" Section of HPB Surger, Washington University School of Medicine, St. Louis MO, Presented at AHPBA, Feb. 2001.

Johnson et al. "Evaluation of the LigaSure Vessel Sealing System in Hemorrhoidectormy" American College of Surgeons (ACS) Clinicla Congress Poster (2000).

Sayfan et al. "Sutureless Closed Hemorrhoidectomy: A New Technique" Annals of Surgery vol. 234 No. 1 Jul. 2001 pp. 21-24.

Heniford et al. "Initial Results with an Electrothermal Bipolar Vessel Sealer" Surgical Endoscopy (2000) 15:799-801.

Heniford et al. "Initial Research and Clinical Results with an Electrothermal Bipolar Vessel Sealer" Oct. 1999.

McLellan et al. "Vessel Sealing for Hemostasis During Pelvic Surgery" Int'l Federation of Gynecology and Obstetrics FIGO World Congress 2000, Washington, D.C.

Levy et al. "Use of a New Energy-based Vessel Ligation Device During Vaginal Hysterectomy" Int'l Federation of Gynecology and Obstetrics (FIGO) World Congress 1999.

Crawford et al. "Use of the LigaSure Vessel Sealing System in Urologic Cancer Surger" Grand Rounds in Urology 1999 vol. 1 Issue 4 pp. 10-17.

Rothenberg et al. "Use of the LigaSure Vessel Sealing System in Minimally Invasive Surgery in Children" Int'l Pediatric Endosurgery Group (IPEG) 2000.

Palazzo et al. "Randomized clinical trial of Ligasure versus open haemorrhoidectomy" British Journal of Surgery 2002, 89, 154-157.

"Innovations in Electrosurgery" Sales/Product Literature; Dec. 31, 2000.

LigaSure Vessel Sealing System, the Seal of Confidence in General, Gynecologic, Urologic, and Laparaoscopic Surgery Sales/Product Literature; Jan. 2004.

Carbonell et al., "Comparison of theGyrus PlasmaKinetic Sealer and the Valleytab LigaSure Device in the Hemostasis of Small, Medium, and Large-Sized Arteries" Carolinas Laparoscopic and Advanced Surgery Program, Carolinas Medical Center, Charlotte, NC 2003.

"Reducing Needlestick Injuries in the Operating Room" Sales/Product Literature 2001.

Chung et al., "Clinical Experience of Sutureless Closed Hemorrhoidectomy with LigaSure" Diseases of the Colon & Rectum vol. 46, No. 1 Jan. 2003.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Paul G. Horgan, "A Novel Technique for Parenchymal Division During Hepatectomy" The American Journal of Surgery, vol. 181, No. 3, Apr. 2001 pp. 236-237.

W. Scott Helton, "LigaSure Vessel Sealing System: Revolutionary Hemostasis Product for General Surgery" Sales/Product Literature 1999.

Michael Choti, "Abdominoperineal Resection with the LigaSure Vessel Sealing System and LigaSure Atlas 20 cm Open Instrument" Innovations That Work, Jun. 2003.

Craig Johnson, "Use of the LigaSure Vessel Sealing System in Bloodless Hemorrhoidectomy" Innovations That Work, Mar. 2000.

Muller et al., "Extended Left Hemicolectomy Using the LigaSure Vessel Sealing System" Innovations That Work, Sep. 1999.
Herman et al. "Laparoscopic Intestinal Resection With the LigaSure Vessel Sealing System: A Case Report" Innovations That Work, Feb. 2002.
Carus at al., "Initial Experience With the LigaSure Vessel Sealing System in Abdominal Surgery" Innovations That Work, Jun. 2002.
Levy at al. "Randomized Trial of Suture Versus Electrosurgical Bipolar Vessel Sealing in Vaginal Hysterectomy" Obstetrics & Gynecology, vol. 102, No. 1, Jul. 2003.
Levy et al., "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.
McLellan et al. "Vessel Sealing for Hemostasis During Gynecologic Surgery" Sales/Product Literature 1999.
Sengupta et al., "Use of a Computer-Controlled Bipolar Diathermy System in Radical Prostatectomies and Other Open Urological Surgery" ANZ Journal of Surgery (2001) 71.9 pp. 538-540.
Olsson et al. "Radical Cystectomy in Females" Current Surgical Techniques in Urology, vol. 14, Issue 3, 2001.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hitar Vessels in Laparoscopic Nephrectomy" Sales/Product Literature 2000.
E. David Crawford "Evaluation of a New Vessel Sealing Device in Urologic Cancer Surgery" Sales/Product Literature 2000.
Joseph Ortenberg "LigaSure System Used in Laparoscopic 1st and 2nd Stage Orchiopexy" Innovations That Work, Nov. 2002.
Koyle et al., "Laparoscopic Palomo Varicocele Ligation in Children and Adolescents" Pediatric Endosurgery & Innovative Techniques, vol. 6, No. 1, 2002.
Dulemba at al. "Use of a Bipolar Electrothermal Vessel Sealer in Laparoscopically Assisted Vaginal Hysterectomy" Sales/Product Literature; Jan. 2004.
Johnson et al. "Evaluation of a Bipolar electrothermal Vessel Sealing Device in Hemorrhoidectomy" Sales/Product Literature; Jan. 2004.
Int'l Search Report PCT/US98/18640 dated Dec. 17, 1998.
Int'l Search Report PCT/US98/23950 dated Dec. 29, 1998.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report EP 98944778 dated Oct. 31, 2000.
Int'l Search Report EP 98958575.7 dated Sep. 20, 2002.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 04013772 dated Apr. 1, 2005.
Int'l Search Report EP 05013463.4 dated Sep. 28, 2005.
Int'l Search Report EP 05013895 dated Oct. 14, 2005.
Int'l Search Report EP 05016399 dated Jan. 5, 2006.
Int'l Search Report EP 05017281 dated Nov. 16, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended—EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Int'l Search Report EP 06005185.1 dated Apr. 18, 2006.
Int'l Search Report EP 06006716 dated Aug. 4, 2006.
Int'l Search Report EP 06008779.8 dated Jun. 13, 2006.
Int'l Search Report EP 1683496 dated Jun. 13, 2006.
Int'l Search Report EP 06014461.5 dated Oct. 20, 2006.
Int'l Search Report EP 06020584.6 dated Jan. 12, 2007.
Int'l Search Report EP 06020583.8 dated Jan. 30, 2007.
Int'l Search Report EP 06020756.0 dated Feb. 5, 2007.
Int'l Search Report EP 06024123.9 dated Feb. 26, 2007.
Int'l Search Report EP 06 020574.7 dated Sep. 21, 2007.
Intl Search Report EP 07 010672.9 dated Oct. 1, 2007.
Int'l Search Report EP 07 013779.9 dated Oct. 18, 2007.
Int'l Search Report EP 07 009026.1 dated Sep. 12, 2007.
Int'l Search Report EP 07 015601.3 dated Dec. 6, 2007.
Int'l Search Report EP 07 015191.5 dated Dec. 19, 2007.
Int'l Search Report EP 07 020283.3 dated Jan. 16, 2008.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Crouch et al. "A Velocity-Dependent Model for Needle Insertion in Soft Tissue" MICCAI 2005; LNCS 3750 pp. 624-632, Dated: 2005.
Int'l Search Report EP 98957771 dated Aug. 9, 2001.
Int'l Search Report EP 05002671.5 dated Dec. 22, 2008.
Int'l Search Report EP 05002674.9 dated Jan. 16, 2009.
Int'l Search Report EP 05019429.9 dated May 6, 2008.
Int'l Search Report EP 06008515.6 dated Jan. 8, 2009.
Int'l Search Report EP 07 014016 dated Jan. 28, 2008.
Int'l Search Report EP 07 021646.0 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 Dated Jun. 15, 2009.
Int'l Search Report EP 09 152898.4 Dated Jun. 10, 2009.
Int'l Search Report PCT/US98/24281 dated Feb. 22, 1999.
Int'l Search Report PCT/US03/28534 dated Dec. 19, 2003.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.
Int'l Search Report EP 04 752343.6 dated Jul. 20, 2007.
Int'l Search Report EP 06 024122.1 dated Mar. 19, 2007.
Int'l Search Report EP 07 001480.8 dated Apr. 12, 2007.
Int'l Search Report EP 07 001488.1 dated May 29, 2007.
Int'l Search Report—Extended EP 07 009029.5 dated Jul. 12, 2007.
Int'l Search Report EP 07 009321.6 dated Aug. 17, 2007.

* cited by examiner

FORCEPS WITH SPRING LOADED END EFFECTOR ASSEMBLY

CROSS-REFERENCE TO RELATED APPLICATIONS

This application claims the benefits of and priority to U.S. patent application Ser. No. 10/937,455 entitled "FORCEPS WITH SPRING LOADED END EFFECTOR ASSEMBLY", now U.S. Pat. No. 7,195,631, which was filed on Sep. 9, 2004, the entire contents of which are hereby incorporated by reference herein.

BACKGROUND

1. Technical Field

The present disclosure relates to endoscopic surgical instruments and, more particularly, to an end effector assembly for use in connection with endoscopic instruments for grasping, sealing, dividing and/or dissecting tissue.

2. Background of Related Art

A hemostat or forceps is a simple pliers-like tool which uses mechanical action between its jaws to constrict vessels and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize and/or seal tissue.

Over the last several decades, more and more surgeons are complimenting traditional open methods of gaining access to vital organs and body cavities with endoscopes and endoscopic instruments which access organs through small puncture-like incisions. Endoscopic instruments are inserted into the patient through a cannula, or port, that has been made with a trocar. Typical sizes for cannula range from three millimeters to twelve millimeters. Smaller cannulas are usually preferred, which, as can be appreciated, ultimately presents a design challenge to instrument manufacturers who must find ways to make surgical instruments that fit through the particularly-sized cannulas.

Certain endoscopic surgical procedures require cutting blood vessels or vascular tissue. However, due to space limitations surgeons can have difficulty suturing vessels or performing other traditional methods of controlling bleeding, e.g., clamping and/or tying-off transected blood vessels. Blood vessels, in the range below two millimeters in diameter, can often be closed using standard electrosurgical techniques. However, if a larger vessel is severed, it may be necessary for the surgeon to convert the endoscopic procedure into an open-surgical procedure and thereby abandon the benefits of laparoscopy.

Several journal articles have disclosed methods for sealing small blood vessels using electrosurgery. An article entitled *Studies on Coagulation and the Development of an Automatic Computerized Bipolar Coagulator*, J. Neurosurg., Volume 75, Jul. 1991, describes a bipolar coagulator which is used to seal small blood vessels. The article states that it is not possible to safely coagulate arteries with a diameter larger than 2 to 2.5 mm. A second article, entitled *Automatically Controlled Bipolar Electrocoagulation—"COA-COMP"*, Neurosurg. Rev. (1984), pp. 187-190, describes a method for terminating electrosurgical power to the vessel so that charring of the vessel walls can be avoided.

As mentioned above, by utilizing an electrosurgical forceps, a surgeon can either cauterize, coagulate/desiccate and/or simply reduce or slow bleeding, by controlling the intensity, frequency and duration of the electrosurgical energy applied through the jaw members to the tissue. The electrode of each jaw member is charged to a different electric potential such that when the jaw members grasp tissue, electrical energy can be selectively transferred through the tissue.

In order to effect a proper seal with larger vessels, two predominant mechanical parameters must be accurately controlled: the pressure applied to the vessel; and the gap distance between the electrically conductive surfaces. More particularly, accurate application of pressure is important to oppose the walls of the vessel; to reduce the tissue impedance to a low enough value that allows enough electrosurgical energy through the tissue; to overcome the forces of expansion during tissue heating; and to contribute to the end tissue thickness which is an indication of a good seal. It has been determined that a typical fused vessel wall is optimum between about 0.001 and about 0.006 inches. Below this range, the seal may shred or tear and above this range the lumens may not be properly or effectively sealed.

With respect to smaller vessels, the pressure applied to the tissue tends to become less relevant whereas the gap distance between the electrically conductive surfaces becomes more significant for effective sealing. In other words, the chances of the two electrically conductive surfaces touching during activation increases as the vessels become smaller.

Various known electrosurgical instruments and methods may occasionally be able to seal larger vessels using an appropriate electrosurgical power curve, coupled with an instrument capable of applying a large closure force to the vessel walls, however, these instruments and methods rarely provide consistent and accurate vessel sealing. Moreover, the process of coagulating small vessels is fundamentally different than electrosurgical vessel sealing. For the purposes herein, "coagulation" is defined as a process of desiccating tissue wherein the tissue cells are ruptured and dried. "Vessel sealing" or "Tissue Sealing" is defined as the process of liquefying the collagen in the tissue so that it reforms into a fused mass. Thus, coagulation of small vessels is sufficient to permanently close the vessels but not necessarily seal the vessels. Larger vessels need to be sealed to assure permanent closure.

Many known electrosurgical instruments include blade members or shearing members which simply cut tissue in a mechanical and/or electromechanical manner and are relatively ineffective for vessel sealing purposes. Other instruments rely on clamping pressure alone to procure proper sealing thickness and are not designed to take into account gap tolerances and/or parallelism and flatness requirements which are parameters which, if properly controlled, can assure a consistent and effective tissue seal. For example, it is known that it is difficult to adequately control thickness of the resulting sealed tissue by controlling clamping pressure alone for either of two reasons: 1) if too much force is applied, there is a possibility that the two poles will touch and energy will not be transferred through the tissue resulting in an ineffective seal; or 2) if too low a force is applied the tissue may prematurely move prior to activation and sealing and/or a thicker, less reliable seal may be created.

As mentioned above, in order to properly and effectively seal larger vessels or tissue, a greater closure force between opposing jaw members is required. It is known that a large closure force between the jaws typically requires a large moment about the pivot for each jaw. This presents a challenge because the jaw members are typically affixed with pins which are positioned to have a small moment arms with respect to the pivot of each jaw member. A large force, coupled with a small moment arm, is undesirable because the large forces may shear the pins. As a result, designers must compensate for these large closure forces by either designing instruments with metal pins and/or by designing instruments which at least partially offload these closure forces to reduce the chances of mechanical failure (see, for example, commonly owned U.S. Pat. No. 6,585,735). As can be appreciated, if metal pivot pins are employed, the metal pins must be insulated to avoid the pin acting as an alternate current path between the jaw members which may prove detrimental to effective sealing.

Increasing the closure forces between electrodes may have other undesirable effects, e.g., it may cause the opposing electrodes to come into close contact with one another which may result in a short circuit and a small closure force may cause pre-mature movement of the issue during compression and prior to activation.

Typically and particularly with respect to endoscopic electrosurgical procedures, once a vessel or tissue is sealed, the surgeon has to remove the sealing instrument from the operative site, substitute a new instrument through the cannula and accurately sever the vessel or tissue along the newly formed seal. As can be appreciated, this additional step may be both time consuming (particularly when sealing a significant number of vessels or tissue) and may contribute to imprecise separation of the vessels or tissue along the sealing line due to the misalignment or misplacement of the severing instrument along the center of the sealing line.

Several attempts have been made to design an instrument which incorporates a knife or blade member which effectively severs the tissue after forming a tissue seal. For example, U.S. Pat. No. 5,674,220 to Fox et al. discloses a transparent instrument which includes a longitudinally reciprocating knife which severs the tissue once sealed. The instrument includes a plurality of openings which enable direct visualization of the tissue during the sealing and severing process. This direct visualization allows a user to visually and manually regulate the closure force and gap distance between jaw members to reduce and/or limit certain undesirable visual effects known to occur when sealing vessels, e.g., thermal spread, charring, etc. As can be appreciated, the overall success of creating an effective tissue seal with this instrument is greatly reliant upon the user's expertise, vision, dexterity, and experience in judging the appropriate closure force, gap distance and length of reciprocation of the knife to uniformly, consistently and effectively seal and separate the tissue at the seal along an ideal cutting plane.

U.S. Pat. No. 5,702,390 to Austin et al. discloses a vessel sealing instrument which includes a triangularly-shaped electrode which is rotatable from a first position to seal tissue to a second position to cut tissue. Again, the user must rely on direct visualization and expertise to control the various effects of sealing and cutting tissue.

Some systems utilize rigid-faced jaw members to provide the necessary closure force to coagulate tissue. These instruments typically rely on drive rod or pull rod to carry the longitudinal force to maintain consistent and repeatable pressure between the jaw members to effectively clamp or coagulate tissue (e.g., a spring actuated pull rod disposed in the handle which provides the necessary clamping force).

Still other systems utilize arcuately-shaped, wire-like jaw members which cooperate with a closure tube to grasp tissue for dissection and coagulation. It is believed that these wire-like jaw frames are not designed to seal tissues since, by and large, the jaw frames do not provide the forces necessary to effect consistent and accurate vessel sealing.

Thus, a need exists to develop an endoscopic electrosurgical instrument which provides the necessary closure forces to seal vessels and other vascular tissue and, when activated, effectively and consistently seals and separates the vessel or the tissue along the seal.

SUMMARY

The present disclosure relates to an endoscopic forceps for treating tissue including a handle assembly and an end effector assembly. The handle assembly has an elongated shaft extending therefrom. The elongated shaft is movable relative to the handle assembly by an actuator. The end effector assembly is attached to a distal end of the elongated shaft and has first and second jaw members. The jaw members are movable about a pivot from a first position in a spaced relation relative to one another to a second position for clamping tissue. Each of the jaw members includes an insulative housing and a flange. The insulative housing has an electrically conductive, inwardly facing tissue contacting surface. The flange has at least one camming surface. The flange includes a spring-like tail which mounts at least partially within the distal end of the elongated shaft to bias the jaw members in an open configuration. A proximal portion of the spring-like tail is biased radially outward within the distal end of the elongated shaft. The actuator is movable relative to the handle to actuate the elongated shaft from a first position wherein the elongated shaft remains proximal to the flanges of the jaw members and the jaw members are biased in a open configuration to at least one subsequent position wherein the distal end of the elongated shaft cams the flanges to pivot the jaw members toward the second position to clamp tissue.

In an embodiment of the present disclosure, the flanges of the jaw members cooperate with the distal end of the elongated shaft to provide a clamping pressure within the range of at least about 3 $kg/cm^2$ to effectively seal tissue upon application of electrosurgical energy.

It is envisioned for the flanges of the jaw members to include sloped forward surfaces which cooperate with the distal end of the elongated shaft to maintain the jaw members in the second position.

In an exemplary embodiment of the disclosure, clamping pressure is maintained within the range of at least about 3 $kg/cm^2$ once the distal end of the elongated shaft translates over the forward surfaces of the flanges.

In an embodiment of the present disclosure, an endoscopic forceps for treating tissue is provided. The forceps of this embodiment includes a handle assembly, an end effector assembly and a knife actuator. The handle assembly has an elongated shaft extending from it. The shaft is movable relative to the handle assembly by an actuator. The end effector assembly is attached to a distal end of the shaft and includes first and second jaw members. The jaw members are movable about a pivot from a first position in a spaced relation to one another to a second position for clamping tissue. The knife actuator advances a knife through tissue held between the jaw members. Each of the jaw members includes an insulative housing, a flange and a knife channel. The insulative housing has an electrically conductive, inwardly facing tissue contacting surface. The flange has at least one camming surface. The flange also includes a spring-like tail which mounts at least partially within the distal end of the elongated shaft to bias the jaw members in an open configuration. A proximal portion of the spring-like tail is biased radially outward within the distal end of the elongated shaft. The actuator is movable relative to the handle to actuate the elongated shaft from a first position where the elongated shaft remains proximal to the flanges of the jaw members and the jaw members are biased in an open configuration to at least one subsequent position where the distal end of the elongated shaft cams the flanges to pivot the jaw members toward the second position to clamp tissue

BRIEF DESCRIPTION OF THE DRAWINGS

By way of example only, embodiments of the endoscopic instrument of the present disclosure will be described with reference to the accompanying drawings, in which.

DETAILED DESCRIPTION

Figure 1A:
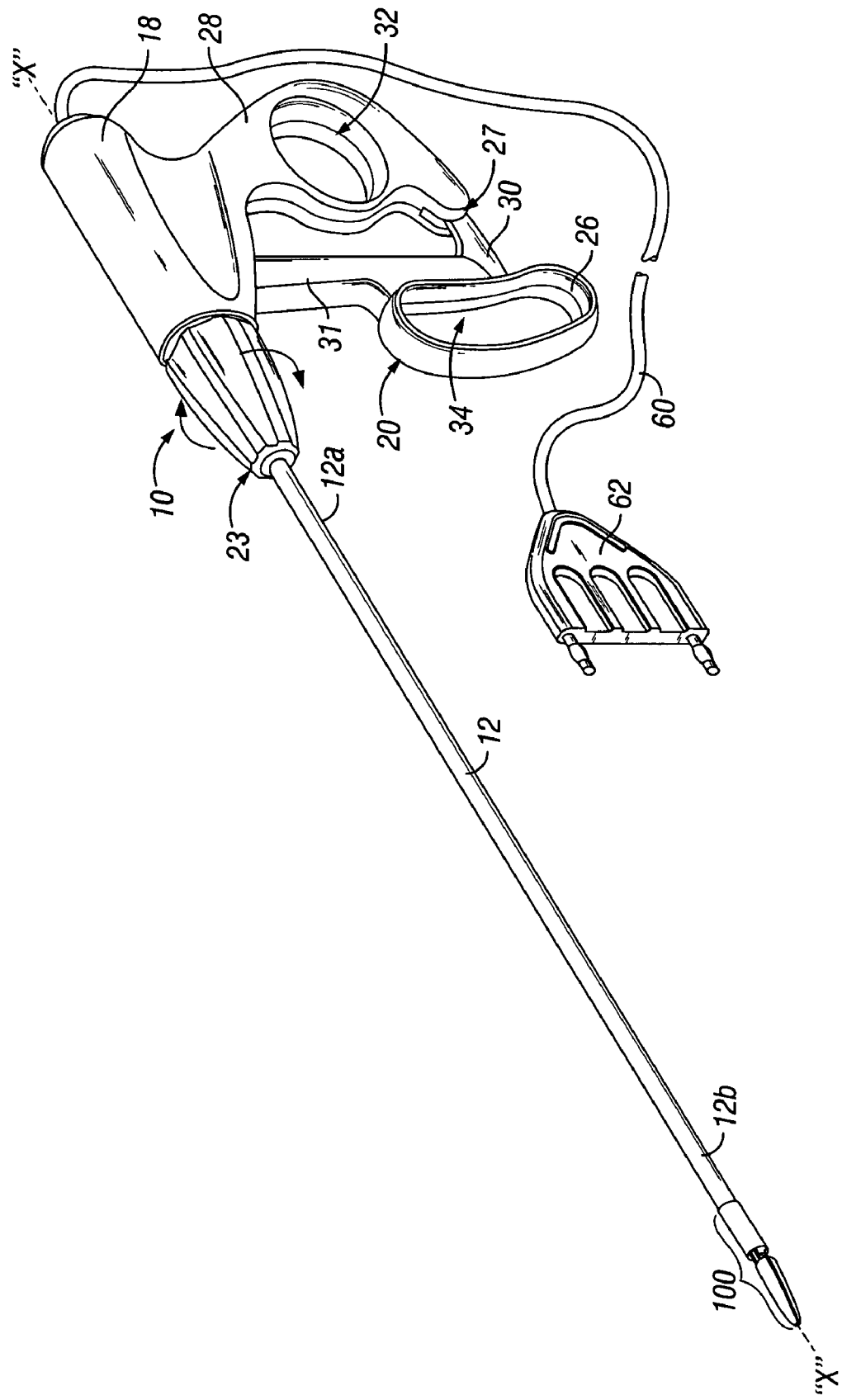
FIG. 1A is a perspective view of an endoscopic instrument according to one embodiment of the present disclosure.

Detailed embodiments of the presently disclosed instruments, devices and systems will now be described in detail with reference to the drawing figures wherein like reference numerals identify similar or identical elements. In the drawings and in the description which follows, the term "proximal", as is traditional, will refer to the end of the instrument, device and/or system which is closest to the operator while the term "distal" will refer to the end of the instrument, device and/or system which is furthest from the operator.

Referring to FIG. 1A, an endoscopic instrument according to one embodiment of the present disclosure is designated generally as reference numeral 10. Endoscopic instrument 10 includes an elongated shaft 12 which is mechanically coupled to a handle assembly 18 at a proximal end 12a thereof and a distal end 12b which is mechanically coupled to an end effector assembly 100. Elongated shaft 12 is preferably hollow and includes internal electrical connections which provide electrical continuity to the end effector assembly 100 as described in more detail below.

End effector assembly 100 includes a pair of opposing jaw members 110 and 120 which are operatively associated with the distal end 12b of elongated shaft 12. Preferably, handle assembly 18 mechanically engages proximal end 12a of shaft 12 and includes an activator 20 for imparting movement to the jaw members 110 and 120 from an open position wherein jaw members 110 and 120 are disposed in spaced relation relative to one another, to a clamping or closed position wherein jaw members 110 and 120 cooperate to grasp tissue therebetween.

With continued reference to FIG. 1A, activator 20 includes a movable handle 26 having an aperture 34 defined therethrough for receiving at least one of an operator's fingers and a fixed handle 28 having an aperture 32 defined therein for receiving an operator's thumb. Movable handle 26 is selectively movable from a first position relative to fixed handle 28 to a second position in closer proximity to fixed handle 28 to close jaw members 110 and 120. The specific mechanics of how the actuator 20 moves the jaw members 110 and 120 from the open to close positions is discussed in more detail below with reference to FIGS. 1B and 1C. The internal mechanically cooperating components associated with longitudinally translating the elongated shaft 12 (or another tube concentrically disposed therein (not shown)) to cam the jaw members 110 and 120 from the open to closed positions is commonly known.

Preferably, fixed handle 28 includes a channel 27 which extends proximally for receiving a ratchet 30 which is coupled to movable handle 26. Ratchet 30 is preferably designed to allow a user to progressively lock, at multiple positions, and subsequently release movable handle 26 relative to fixed handle 28. The handle structure, in turn, allows for the progressive closure of end effector assembly 100 as well as locking engagement of opposing jaw members 110, 120. In some cases it may be preferable to include other mechanisms to control and/or limit the movement of handle 26 relative handle 28, such as, for example, hydraulic, semi-hydraulic and/or gearing systems.

In one particular embodiment according to the present disclosure, a ratchet is not included for selectively locking the jaw members 110 and 120 relative to one another and to maintain the pressure between jaw members 110 and 120. In this particular embodiment, the forceps 10 relies on the operating characteristics of the jaw members 110 and 120 and elongated tube 12 which, when moved into the closed position, will automatically maintain the two jaw members 110 and 120 engaged about tissue within the preferred pressure range to effectively seal tissue. As explained below with reference to FIGS. 1B, 1C and 2, the particular configuration of each jaw member 110 and 120 is designed to close upon distal advancement of the elongated tube 12 and also maintain pressure between the jaw members 110 and 120 until the handle 26 is re-actuated to open the jaw members 110 and 120 relative to one another. Thus, ratchet 30 in this instance is not necessary and may simply be utilized to guide handle 26 relative to handle 28.

Desirably, handle 28 includes a rotating assembly 23 for controlling the rotational movement of end effector assembly 100 about a longitudinal axis "X" defined along elongated shaft portion 12. In use, as rotating assembly 23 is rotated about the longitudinal "X" axis, end effector assembly 100 is correspondingly rotated about the longitudinal "X" axis. One such type of rotating assembly 23 is disclosed in commonly-owned U.S. patent application Ser. No. 10/472,295 entitled "VESSEL SEALER AND DIVIDER" and U.S. patent application Ser. No. 10/460,926 entitled "VESSEL SEALER AND DIVIDER FOR USE WITH SMALL TROCARS AND CANNULAS" the contents of both of these applications being incorporated by reference herein in their entirety.

As best seen in FIG. 1A, forceps 10 also includes an electrosurgical connector 62 which connects the forceps 10 to a source of electrosurgical energy, e.g., a generator (not shown) by virtue of a cable lead 60. Preferably, generators such as those sold by Valleylab—a division of Tyco Healthcare LP, located in Boulder, Colo. are used as a source of electrosurgical energy, e.g., FORCE EZ™ Electrosurgical Generator, FORCE FX™ Electrosurgical Generator, FORCE 1C™, FORCE 2™ Generator, SurgiStat™ II. One such system is described in commonly-owned U.S. Pat. No. 6,033,399 entitled "ELECTROSURGICAL GENERATOR WITH ADAPTIVE POWER CONTROL" the entire contents of which are hereby incorporated by reference herein. Other systems have been described in commonly-owned U.S. Pat. No. 6,187,003 entitled "BIPOLAR ELECTROSURGICAL INSTRUMENT FOR SEALING VESSELS", U.S. patent application Ser. No. 10/427,832 entitled "METHOD AND SYSTEM FOR CONTROLLING OUTPUT OF RF MEDICAL GENERATOR" and U.S. patent application Ser. No. 10/626,390 entitled "VESSEL SEALING SYSTEM" the entire contents of all of which are also incorporated by reference herein.

Figure 1B:
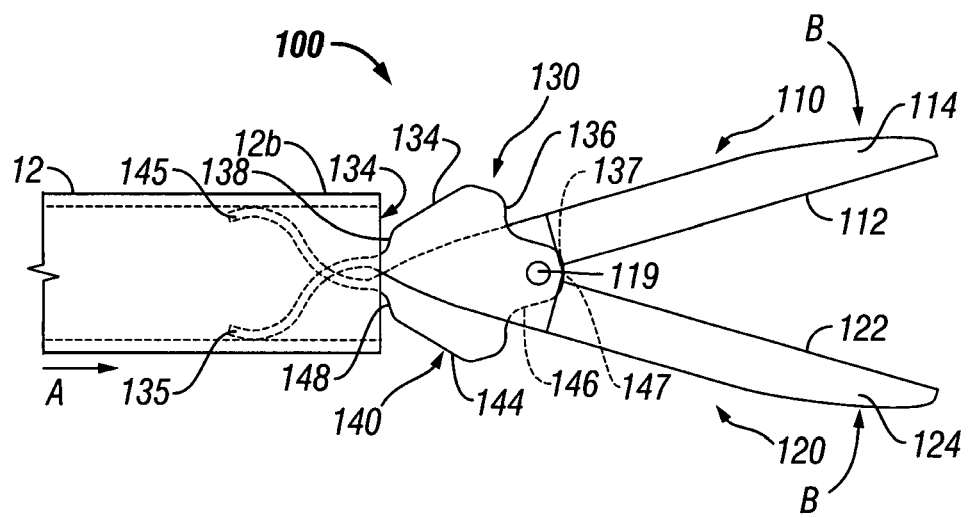
FIG. 1B is an enlarged, side view of an end effector assembly of the endoscopic instrument of FIG. 1A shown in an open configuration.
Figure 1C:
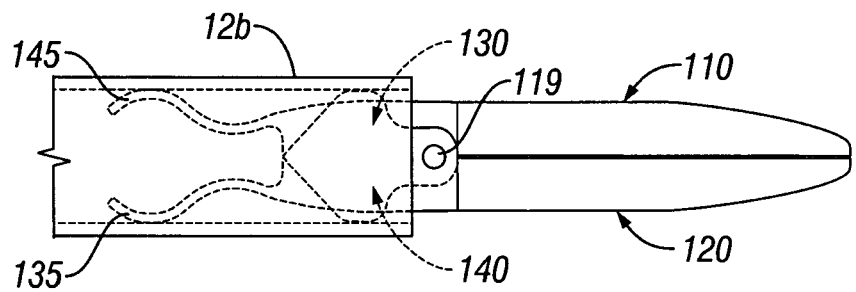
FIG. 1C is an enlarged, side view of an end effector assembly of the endoscopic instrument of FIG. 1A shown in a closed configuration.
Figure 2:
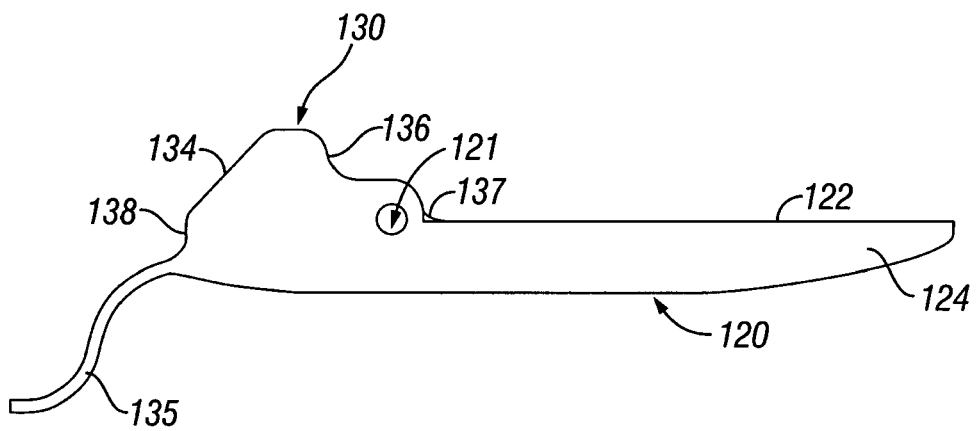
FIG. 2 is a side, elevational view of the bottom jaw member of FIG. 1B.

With reference to FIGS. 1B, 1C and 2, end effector assembly 100 includes a first jaw member 110 and a second jaw member 120 which are movable from an open position to a closed position by movement of handle assembly 18 as described above. Jaw members 110 and 120 are generally symmetrical and include similar component features which cooperate to permit facile rotation about a pivot pin 119 to effect opening and closing of end effector assembly 100. As a result, and unless otherwise noted, only second jaw member 120 (shown in FIG. 2) and the operative features associated therewith are described in detail herein but as can be appreciated, many of these features apply to first jaw member 110 as well.

Jaw member 120 includes a jaw housing 124 having a flange 130 extending proximally therefrom. Flange 130 includes a pivot hole 121 formed therethrough for receiving pivot pin 119 (see FIG. 1B). Jaw housing 124 of jaw member 120 includes an electrically conductive tissue contacting surface 122 disposed on an inner facing surface thereof which aligns with a corresponding electrically conductive tissue contacting surface 112 of jaw member 110 when the jaw members 110 and 120 are moved to the closed position (see FIG. 1C). It is envisioned that the electrically conductive surface 122 may be integrally associated with the jaw housing 124 or engaged in some known mechanical fashion, e.g., by stamping, by overmolding, by overmolding a stamped plate, snap-fit, sonic welding and/or by overmolding a metal injection molded plate or other ways customary in the trade. Mounting the electrically conductive surface 122 to the jaw housing 124 in any one of these fashions is known to effectively reduce the thermal spread to adjacent tissue structures during and/or immediately following activation. The electrically conductive surface 122 may also include a pinch trim (not shown) which facilitates secure engagement of the electrically conductive surface 122 to the insulating housing 124 and also simplifies the overall manufacturing process.

As mentioned above, jaw member 120 includes a proximal flange 130 which is configured and dimensioned to cooperate with a proximal flange 140 of jaw member 110 to facilitate actuation of the jaw members 110 and 120 from the open to close positions when handle 26 is moved relative to fixed handle 28. More particularly and as best shown in FIG. 2, proximal flange 130 has a shaped profile which includes forward ski-slope like surfaces 136 and 137 and a rear inclined surface 134 which are designed to cooperate with the distal end 12b of the elongated shaft 12 to close, lock and maintain the jaw members 110 and 120 about the tissue within the predefined working pressure ranges for sealing tissue of about 3 kg/cm² to about 16 kg/cm². Flange 130 also includes a rear ski-slope like surface 138 which is designed to facilitate engagement of the distal end 12b of shaft 12 with the flange 130.

Jaw member 120 also includes a tail-like spring 135 which extends proximally from flange 130 and is designed to abuttingly engage an inner peripheral surface 13 of the distal end 12b elongated shaft 12. When jaw member 120 is mechanically engaged within surface 13 of the distal end 12b of shaft 12, spring 135 biases jaw member 120 in an open configuration prior to distal advancement of the elongated shaft 12.

As mentioned above, jaw member 110 includes similar elements to jaw member 120, i.e., electrically conductive surface 112, insulative jaw housing 114 and flange 140. Flange 140, likewise includes similar elements to flange 130, e.g., forward surfaces 146 and 147, inclined surface 144, rear slope 148 and tail-like spring 145.

Upon distal activation of the elongated shaft 12 in the direction of arrow "A" (See FIG. 1B), the rear slopes 138 and 148 of flanges 130 and 140 guide distal end 12b into the inclined surfaces 134, 144. The distal end 12b then cams the surfaces 134 and 144 against the inner peripheral surface 13 of the distal end 12b of shaft 12 thus forcing the jaw members 110 and 120 closer to one another in the direction of arrow "B" to engage tissue disposed therebetween. Once the jaw members 110 and 120 are fully cammed and closed about the tissue, continued forward movement of the shaft 12 forces the distal end 12b over the forward slope surfaces 136, 137 and 146, 147 which, in turn, lock the distal end 12b atop the flanges 130 and 140 thus maintaining consistent pressure between the two jaw members 110 and 120.

After the sealing process has been completed, the user simply de-actuates the actuator 20 (i.e., moves handle 26 relative to handle 28 in the opposite direction) which retracts the shaft 12 which, in turn, pulls the distal end 12b of the shaft 12 proximally over the forward slopes 137, 136 and 147, 146, respectively, to release the jaw members 110 and 120 from their locked orientation. Continued movement of the actuator 20 retracts the distal end 12b over inclined surfaces 134, 144 to allow the jaw members 110 and 120 to open relative to one another. As can be appreciated, the biasing action of the springs 135 and 145 force the jaw members 110 and 120 to open as the distal end 12b retracts along inclined surfaces 134 and 144. Proximal slopes 138 and 148 are preferably dimensioned to facilitate opening of the jaw members 110 and 120 with respect to one another as the distal end 12b of the shaft 12 is retracted to its proximal-most position.

Preferably, each spring 135, 145 is made from a durable, semi-resilient material which continually provides an adequate force to repeatedly bias the jaw members 110 and 120 to the open position relative to one another during periods of prolonged use. It is envisioned that the proximal sloped surfaces 138 and 148 may be dimensioned to cooperate with the springs 135 and 145 to facilitate opening of the jaw members 110 and 120 upon proximal movement of the shaft 12.

It is envisioned that proximal flanges 130 and 140 are made from a substantially rigid material which can withstand the necessary forces associated with sealing tissue. More particularly and as mentioned above, it is necessary to maintain a closure pressure of about 3 kg/cm² to about 16 kg/cm² between sealing surfaces 112 and 122 to effectively seal tissue during electrical activation. Thus, the cammed surfaces 134 and 144 are preferably made from a substantially durable material which can easily withstand these forces during operational periods of prolonged and repeated use. The proximal flanges 130 and 140 of the jaw members 110 and 120 cooperate with the distal end 12b of the elongated shaft 12 to provide and maintain a clamping pressure within the above working range. Moreover, the clamping pressure is maintained at a point proximal to the pivot 119 which removes the need to provide a pressure-assisting spring (or other mechanically-assisting element) within the handle 18. Once the shaft 12 translates over the forward slopes 136 and 146, the jaw members 110 and 120 lock in the closed position which eliminates the need to provide a ratchet mechanism in the handle to relieve clamping pressure during activation.

Alternatively, it is envisioned that the flange portions 130 and 140 may be made from a semi-compressible material having a specific spring rate (or compression rate) which cooperates with the distal end 12b of the shaft 12 to maintain the jaw members within the specified working range of 3 kgcm$^2$ to about 16 kg/cm$^2$.

It is envisioned that the jaw members 110 and 120 are energized to different potentials when the forceps 10 is configured for bipolar procedures and the same potential for monopolar procedures. With respect to the bipolar configuration, one of the jaw members, e.g., 110, may be adapted to connect to a first potential of an electrosurgical generator (not shown), while the other jaw member, e.g., may be adapted to connect to a second electrical potential to communicate bipolar energy through tissue held therebetween. It is contemplated that one or both of the jaw members 110 and 120 may be adapted to connect to the electrosurgical generator by electrical leads, one or more electrical conductors (e.g., an electrically conductive tube or elongated rod) or in other ways know in the trade. For example, commonly-owned U.S. patent application Ser. No. 10/179,863 entitled "VESSEL SEALER AND DIVIDER", U.S. patent application Ser. No. 10/369,894 entitled "VESSEL SEALER AND DIVIDER AND METHOD FOR MAKING SAME" U.S. patent application Ser. No. 10/246,107 entitled "ENDOSCOPIC BIPOLAR ELECTROSURGICAL FORCEPS" and U.S. patent application Ser. No. 10/460,926 entitled "VESSEL SEALER AND DIVIDER FOR USE WITH SMALL TROCARS AND CANNULAS" include various electrical configurations for supplying the jaw members 110 and 120 with electrosurgical energy to treat tissue, the contents of all of which being hereby incorporated by reference herein.

It is also envisioned that the forceps 10 may be electrically or electro-mechanically configured for both monopolar activation and bipolar activation and may include circuitry and/or various switching arrangements disposed therein (not shown) for accomplishing this purpose. For example, the forceps may include circuitry which allows the surgeon to selectively apply either monopolar energy or bipolar energy depending upon a particular purpose. In this instance, circuitry is preferably included to prevent inadvertent monopolar activation without verification of a return pad (not shown) being in contact with the patient.

Desirably, when in the closed position, end effector assembly 100 defines a gap distance "G" between tissue contact surface 112 of first jaw member 110 and tissue contact surface 122 of second jaw member 120. Preferably, gap distance "G", between opposing tissue contact surfaces 112, 122, ranges from about 0.001 inches to about 0.006 inches and, more preferably, between about 0.002 inches and about 0.003 inches.

Alternatively, one or a series of stop members (not shown) may be employed on the inner facing surfaces of the electrically conductive sealing surfaces 112 and 122 to define the gap "G" between the opposing jaw members 110 and 120. The stop member(s) may also be positioned proximal the pivot 119 or adjacent the electrically conductive surfaces 112 and 122 to define the gap "G". A detailed discussion of these and other envisioned stop members as well as various manufacturing and assembling processes for attaching and/or affixing the stop members to the electrically conductive sealing surfaces are described in commonly assigned, co-pending U.S. application Ser. No. 10/471,818 entitled "VESSEL SEALER AND DIVIDER WITH NON-CONDUCTIVE STOP MEMBERS", which is hereby incorporated by reference in its entirety herein.

It is envisioned that the closure of the jaw members 110 and 120 may be selectively controlled to allow delicate manipulation of fine tissue as need during the course of a particular operation. More particularly, distal translation of the shaft end 12b against flanges 130 and 140 may be regulated to control the relative closure distance between jaw members 110 and 120 and/or control the relative closure force between the jaw members 110 and 120. Moreover, the inclined surfaces 134 and 144 may be dimensioned to enhance the surgeon's level of tactical control during the tissue clamping. Further, moving the jaw members 110 and 120 from the open to closed orientations allows the jaw members 110 and 120 to act as dissectors for separating tissue and other structures during operating conditions.

Turning now to FIGS. 3A-4C, another embodiment of the present disclosure is shown which includes a forceps 300 having an end effector assembly 200 which includes first and second jaw members 210 and 220. The jaw members 210 and 220 are movable from an open position to a closed position by movement of handle assembly 18 as described above. Again, jaw members 210 and 220 are generally symmetrical and include similar component features as described above with respect to FIGS. 1A-2, namely, jaw housings 214 and 224 each having an electrically conductive tissue contacting surface 212 and 222, respectively, flanges 240 and 230, spring-like tails 245 and 235 and a pivot 219.

Figure 3A:
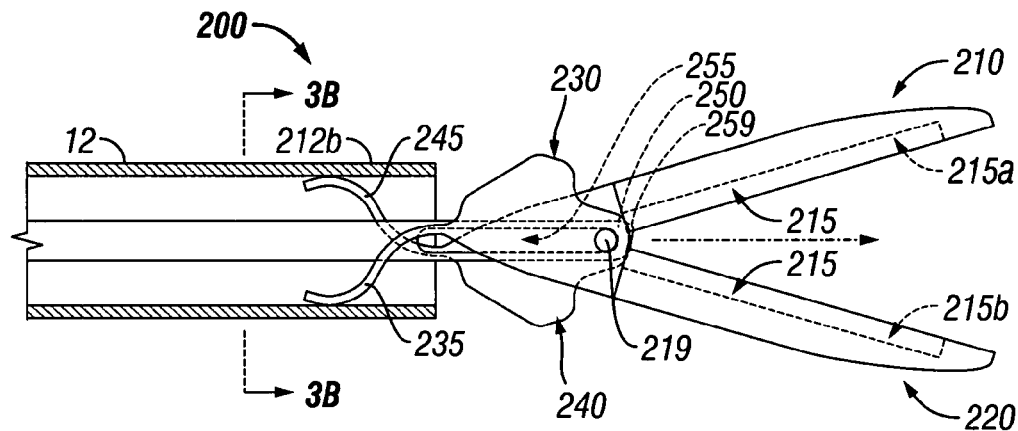
FIG. 3A is a schematically-illustrated, side cross sectional view of an end effector assembly according to another embodiment of the present disclosure shown in an open configuration and incorporating a knife for selectively cutting tissue.
Figure 3B:
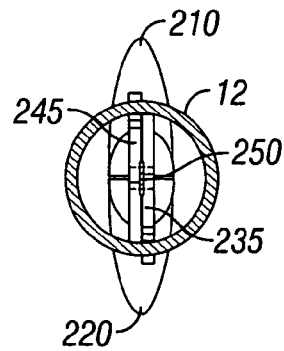
FIG. 3B is a cross sectional view taken along line 3B-3B of FIG. 3A.
Figure 4A:
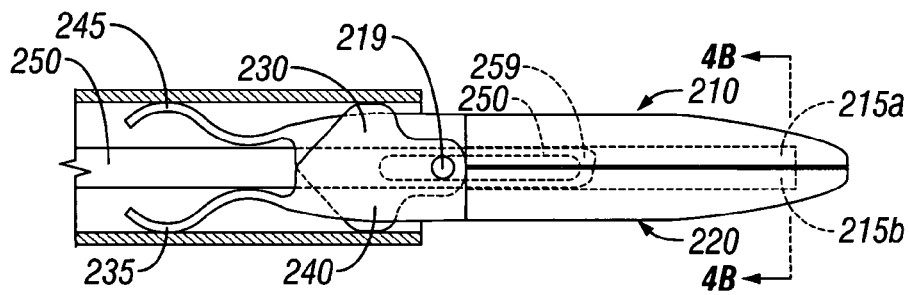
FIG. 4A is a schematically-illustrated side, cross sectional view the embodiment of FIG. 3A shown in a closed configuration.
Figure 4B:
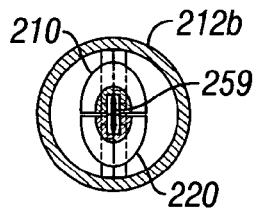
FIG. 4B is a cross sectional view taken along line 4B-4B of FIG. 4A.

Each jaw member 110 and 120 includes an elongated channel 215a and 215b disposed therein which together (i.e., when the jaw members 110 and 120 are disposed in a closed orientation) define a knife channel 215 therebetween. Knife channel 215 is dimensioned to allow selective reciprocation of a knife or cutting edge 250 therethrough. Knife 250 includes an elongated slot 255 defined therein which is dimensioned to facilitate reciprocation of knife 250 within channel 215 and about pivot 219. It is also envisioned that pivot 219 and channel 215 may be appropriately dimensioned to guide knife 250 through channel 215 upon reciprocation thereof. In this particular configuration and as best illustrated in FIGS. 3B and 4B, the spring-like tails 235 and 245 of each jaw member 220 and 210, respectively, are preferably transversally offset relative to the knife 250 to facilitate selective reciprocation of the knife 250 through channel 215.

Figure 4C:
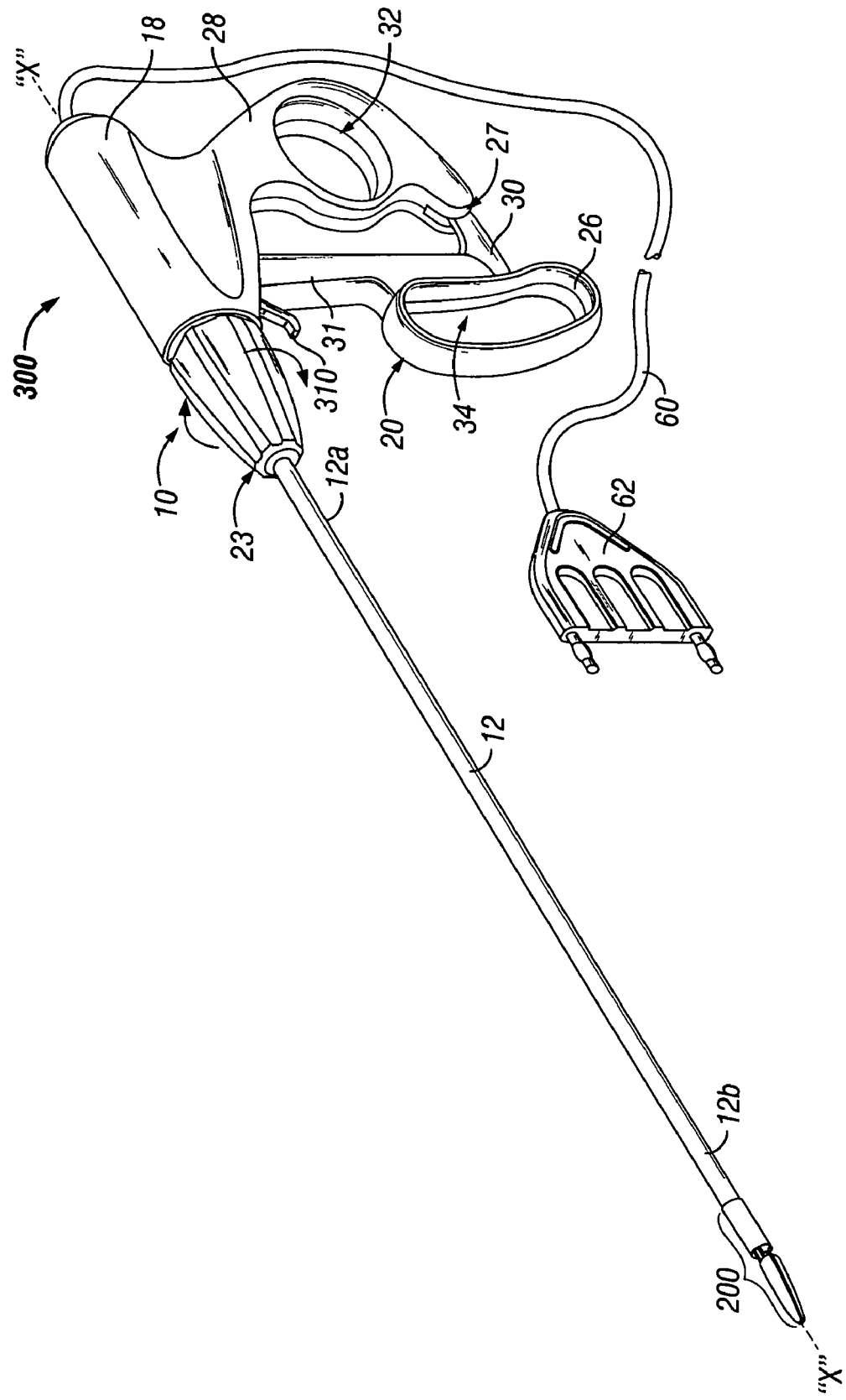
FIG. 4C is a perspective view of an endoscopic forceps according to the present disclosure showing a knife actuator for reciprocating the knife of FIGS. 3A and 4A.

As best shown in FIG. 4C, a knife actuator 310 is included with the forceps 300 and is preferably integrally associated with handle assembly 18. Knife actuator 310 is selectively movable relative to handle assembly 18 from a first position wherein the knife 250 is retracted (i.e., proximally disposed relative to the tissue) to a second position wherein the knife 250 is distally extended through the knife channel 215. It is envisioned that the knife actuator 310 may include a safety mechanism which prevents movement of the knife 250 when the jaw members 110 and 120 are disposed in the open configuration. Commonly-owned U.S. patent application Ser. No. 10/369,894 entitled "VESSEL SEALER AND DIVIDER AND METHOD FOR MAKING SAME", U.S. patent application Ser. No. 10/460,926 entitled "VESSEL SEALER AND DIVIDER FOR USE WITH SMALL TROCARS AND CANNULAS" and U.S. patent application Ser. No. 10/873,860 entitled "OPEN VESSEL SEALING INSTRUMENT WITH CUTTING MECHANISM AND DISTAL LOCKOUT" disclose several different types of safety mechanisms which may be associated with either the handle, housing or end effector assembly to accomplish this purpose, the contents of all of which being incorporated by reference herein in their entirety.

In one embodiment, it is contemplated that knife 250 includes a sharpened distal end 259 which allows the knife 250 to easily navigate through tissue structures disposed between the jaw members 110 and 120 upon activation of the knife actuator 310. Alternatively, the knife 250 may be substantially dull but the knife actuator 310 includes a large cutting force associated therewith such that selective activation of the knife actuator 310 forces the substantially dull blade through the tissue disposed between the jaw members 210 and 220. A spring or other mechanically advantageous element may be utilized to generate the forces necessary to repeatedly navigate the knife 250 through the tissue.

From the foregoing and with reference to the various figure drawings, those skilled in the art will appreciate that certain modifications can also be made to the present disclosure without departing from the scope of the same. For example, while jaw members are shown as being substantially linear, including a substantially linear knife channel formed therein, it is envisioned that jaw members may be arcuate and include arcuate knife channel formed therein. As such, knife may be made from a semi-compliant material or may be multi-segmented to assure consistent, facile and accurate cutting and/or reciprocation through knife channel.

It is envisioned that the outer surface of the end effector assembly may include a nickel-based material, coating, stamping, metal injection molding which is designed to reduce adhesion between the end effector assembly (or components thereof) with the surrounding tissue during operation thereof. Moreover, it is also contemplated that the sealing surfaces of jaw members may be manufactured from one (or a combination of one or more) of the following materials: nickel-chrome, chromium nitride, MedCoat 2000 manufactured by The Electrolizing Corporation of OHIO, inconel 600 and tin-nickel. Sealing surfaces may also be coated with one or more of the above materials to achieve the same result, i.e., a "non-stick surface". Preferably, the non-stick materials are of a class of materials that provide a smooth surface to prevent mechanical tooth adhesions. As can be appreciated, reducing the amount that the tissue "sticks" during sealing improves the overall efficacy of the instrument. Reference may be made to commonly assigned and owned U.S. patent application Ser. No. 10/284,562 entitled "VESSEL SEALING INSTRUMENT", which is hereby incorporated by reference in its entirety herein, for a detailed discussion of the manufacture of the sealing surfaces.

Although many of the instruments described herein may be designed to seal and divide tissue through standard-sized cannula, one envisioned embodiment of the present disclosure includes a reduced-diameter shaft and end effector assembly which is specifically dimensioned to fit through a 5 mm cannula. As can be appreciated, utilizing a smaller-sized surgical instrument can be extremely beneficial to the patient (i.e., reduced trauma, healing and scar tissue).

Preferably, any of the instruments disclosed herein may be designed to be electrically couple to a foot switch (not shown) which allows the surgeon to selectively control the electrosurgical energy transferred to the tissue. In an alternate embodiment, instrument may be activated via a handswitch (not shown) located on the handle assembly. Reference may be made to the above-identified, commonly assigned U.S. patent application Ser. No. 10/460,926 for a detailed discussion of one example of a handswitch which may be utilized with the present disclosure.

It is also envisioned that knife may be energized and/or may be dimensioned as a so called "hot wire" which is selectively activateable by the user to divide the tissue after sealing. More particularly, a separate wire (not shown) may be mounted between the jaw members which is selectively movable and energizable upon activation of a handswitch or footswitch. The hot wire may be configured such that the user can move the wire in an inactivated or activated state which, as can be appreciated, would allow the user to cut the tissue on a reverse stroke if desired.

Although the subject instrument has been described with respect to preferred embodiments, it will be readily apparent to those having ordinary skill in the art to which it appertains that changes and modifications may be made thereto without departing from the spirit or scope of the subject instrument.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An endoscopic forceps for treating tissue, comprising:
a handle assembly having a elongated shaft extending therefrom, the shaft being movable relative to the handle assembly by an actuator;
an end effector assembly attached to a distal end of the shaft, the end effector assembly having first and second jaw members being movable about a pivot from a first position in spaced relation relative to one another to a second position for clamping tissue, a tissue-contacting surface of the first jaw defining a longitudinal plane when the first jaw member is in the second position, each of the jaw members including:
a housing having an electrically conductive, inwardly facing tissue contacting surface;
a flange having at least one camming surface, the flange including a spring-like tail which mounts at least partially within the distal end of the elongated shaft to bias the jaw members in an open configuration, wherein portions of the spring-like tail are on opposite sides of the longitudinal plane when the jaw members are in the open configuration, wherein a proximal portion of the spring-like tail is biased radially outward within the distal end of the elongated shaft;
the actuator being movable relative to the handle to actuate the elongated shaft from a first position wherein the elongated shaft remains proximal to the flanges of the jaw members and the jaw members are biased in an open configuration to at least one subsequent position wherein the distal end of the elongated shaft cams the flanges to pivot the jaw members toward the second position to clamp tissue.

2. An endoscopic forceps according to claim 1, wherein the flanges of the jaw members cooperate with the distal end of the elongated shaft to provide a clamping pressure within the range of at least about 3 kg/cm$^2$ to effectively seal tissue upon application of electro surgical energy.

3. An endoscopic forceps according to claim 2, wherein the flanges of the jaw members include sloped forward surfaces which cooperate with the distal end of the elongated shaft to maintain the jaw members in the second position.

4. An endoscopic forceps according to claim 3, wherein once the distal end of the elongated shaft translates over the forward surfaces of the flanges, clamping pressure is maintained within the range of at least about 3 kg/cm$^2$.

5. An endoscopic forceps for treating tissue, comprising:
a handle assembly having a elongated shaft extending therefrom, the shaft being movable relative to the handle assembly by an actuator;
an end effector assembly attached to a distal end of the shaft, the end effector assembly having first and second jaw members being movable about a pivot from a first position in spaced relation relative to one another to a second position for clamping tissue;
a knife actuator for advancing a knife through tissue held between jaw members;
wherein each of the jaw members includes:
- a housing having an electrically conductive, inwardly facing tissue contacting surface;
- a flange having at least one camming surface, the flange including a spring-like tail which mounts at least partially within the distal end of the elongated shaft to bias the jaw members in an open configuration, wherein portions of the spring-like tail are on opposite sides of the longitudinal plane when the jaw members are in the open configuration, wherein a proximal portion of the spring-like tail is biased radially outward within the distal end of the elongated shaft;

a knife channel for reciprocating the knife therethrough;
the actuator being movable relative to the handle to actuate the elongated shaft from a first position wherein the elongated shaft remains proximal to the flanges of the jaw members and the jaw members are biased in an open configuration to at least one subsequent position wherein the distal end of the elongated shaft cams the flanges to pivot the jaw members toward the second position to clamp tissue.

* * * * *